United States Patent
Miyake

(10) Patent No.: US 7,041,053 B2
(45) Date of Patent: May 9, 2006

(54) ENDOSCOPE PROVIDED WITH A SECTION FOR BENDING THE ENDOSCOPE

(75) Inventor: Kiyoshi Miyake, Asaka (JP)

(73) Assignee: Olympus Optical Co., Ltd., (JP)

( * ) Notice: Subject to any disclaimer, the term of this patent is extended or adjusted under 35 U.S.C. 154(b) by 258 days.

(21) Appl. No.: 10/653,946

(22) Filed: Sep. 4, 2003

(65) Prior Publication Data

US 2004/0049097 A1 Mar. 11, 2004

(30) Foreign Application Priority Data

Sep. 6, 2002 (JP) .............................. 2002-261748

(51) Int. Cl.
*A61B 1/00* (2006.01)

(52) U.S. Cl. ...................... 600/146; 600/118; 600/131; 600/152

(58) Field of Classification Search ................ 600/118, 600/131, 146, 152
See application file for complete search history.

(56) References Cited

U.S. PATENT DOCUMENTS

| 5,159,446 A | | 10/1992 | Hibino et al. |
| 5,400,769 A | | 3/1995 | Tanii et al. |
| 5,431,645 A | * | 7/1995 | Smith et al. .................... 606/1 |
| 5,658,238 A | * | 8/1997 | Suzuki et al. ............... 600/150 |
| 6,551,237 B1 | * | 4/2003 | Matsui ....................... 600/118 |
| 2002/0165430 A1 | * | 11/2002 | Matsui ....................... 600/118 |

FOREIGN PATENT DOCUMENTS

JP 5-15486 1/1993

* cited by examiner

*Primary Examiner*—Beverly M. Flanagan
*Assistant Examiner*—Matthew J. Kasztejna
(74) *Attorney, Agent, or Firm*—Dickstein, Shapiro, Morin & Oshinsky, LLP.

(57) ABSTRACT

An endoscope is provided with a centering control section and a centering button. The centering control section is configured to control a bending mechanism in such a manner as to return a bendable portion to a neutral position where the bendable portion is substantially linear. The centering button is used for entering an instruction for controlling the centering control section. The endoscope is also provided with a personal computer configured to change the bend the bendable portion should have when the bendable portion is returned to the neutral position. The bend is changed in accordance with a bending characteristic variance the bendable portion may undergo in each bending direction.

21 Claims, 17 Drawing Sheets

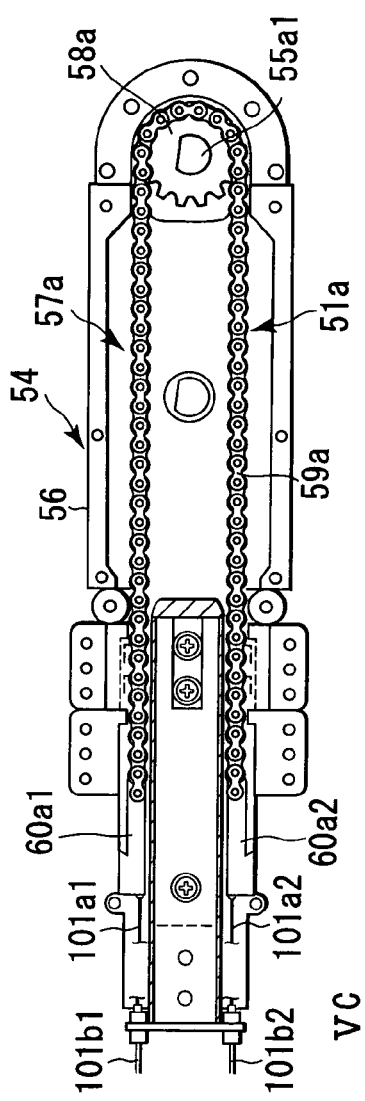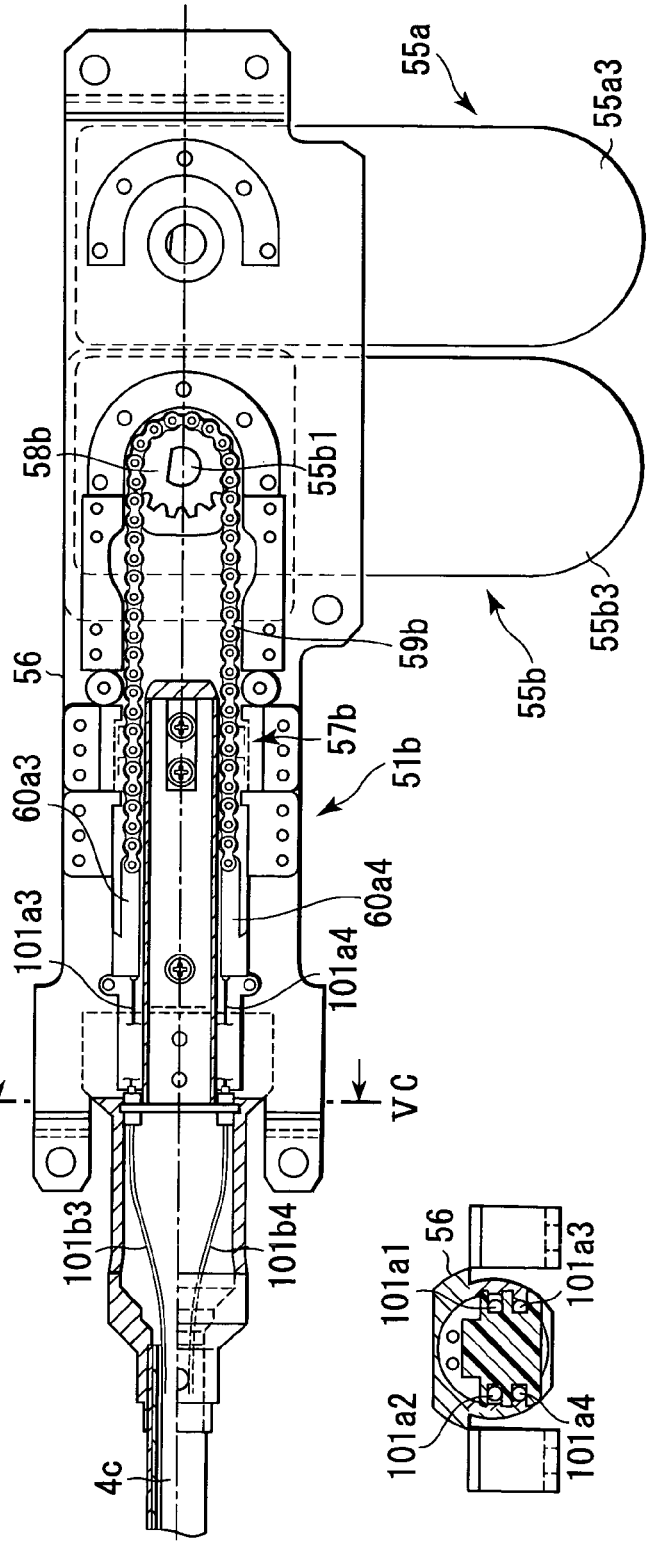
FIG. 5A
FIG. 5B
FIG. 5C

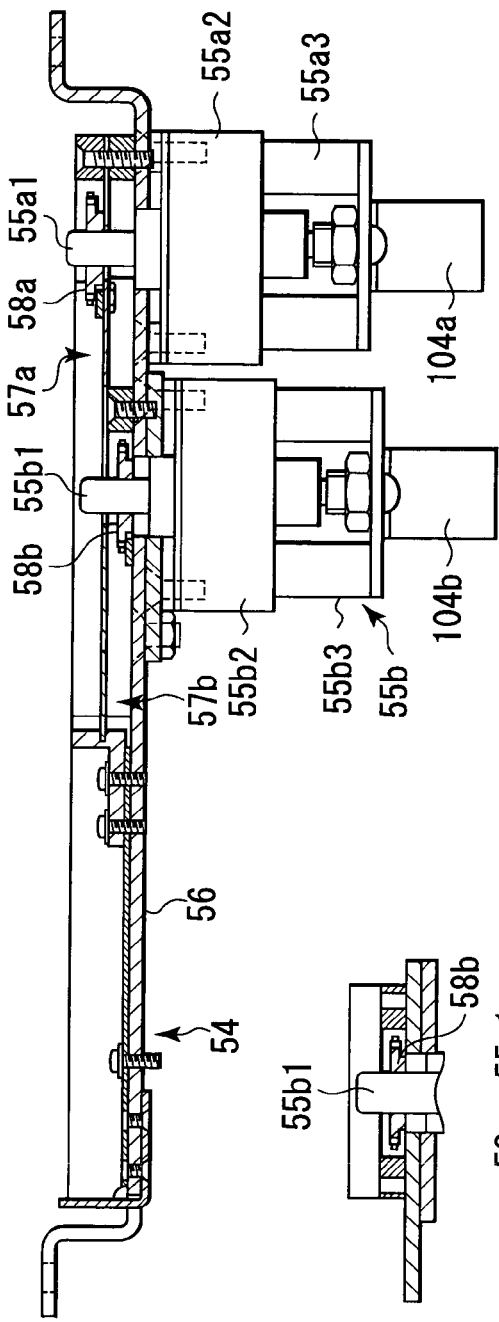
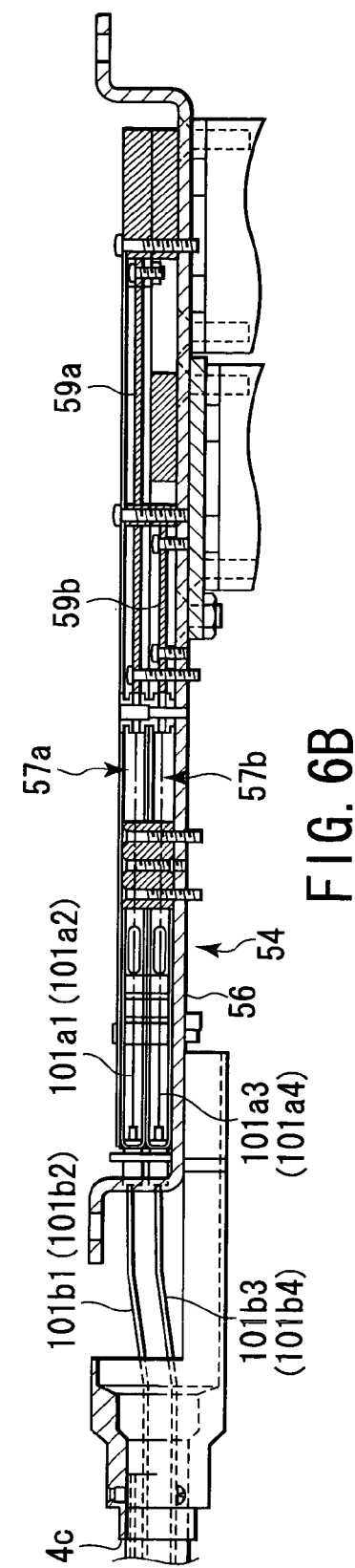
FIG. 6A
FIG. 6B
FIG. 6C
FIG. 6D

ENDOSCOPE PROVIDED WITH A SECTION FOR BENDING THE ENDOSCOPE

CROSS-REFERENCE TO RELATED APPLICATIONS

This application is based upon and claims the benefit of priority from the prior Japanese Patent Application No. 2002-261748, filed Sep. 6, 2002, the entire contents of which are incorporated by reference.

BACKGROUND OF THE INVENTION

1. Field of the Invention

The present invention relates to an endoscope inserted into a space to be inspected and used for observing the space.

2. Description of the Related Art

In general, an endoscope widely used for industrial purposes comprises a flexible insertion section, which is to be inserted into a space to be inspected. The insertion section includes a bendable portion, and this bendable portion can be bent in the vertical direction, in the horizontal direction or in any desired direction, i.e., a combination of the vertical and horizontal directions. A plurality of bending-operation wires (e.g., four wires) are attached to the bendable portion. The proximal end of each bending-operation wire extends toward the proximal portion of the insertion section. An operation section is coupled to the proximal end of the insertion section. The operation section includes a bending-operation mechanism, and the proximal ends of the bending-operation wires are coupled to this bending-operation mechanism.

The operation section includes an input device, such as a joystick. The bending-operation mechanism is driven and the bendable portion is bent, using the joystick. The joystick is provided with a stick whose proximal portion is pivotally supported by a pivot support. The stick is movable between a neutral position where it stands upright and a slanted position where it is slanted. When the stick is slanted in a direction at a desired angle, signals corresponding to the direction and angle of the stick are generated. The joystick outputs signals when operated, and the driving motor or other structural elements of the bending-operation mechanism are driven in accordance with the output signals. The bending-operation wires are pulled, accordingly. In this manner, the bendable portion is bent in association with the pulling movement of each bending-operation wire when the joystick is operated. (An example of this type of endoscope is disclosed, for example, in Jpn. Pat. Appln. KOKAI Publication No. 5-15486.)

In an endoscope of the above structure, the bending-operation wires are inserted in angle coils for protection, and in this state they are arranged in the interior of the tube of the insertion section. When the bending-operation wires are pulled, they slide along the inner surface of the angle coils. When the bendable portion is bent, there is inevitably a certain degree of resistance (e.g., frictional resistance) between the bending-operation wires and the angle coils. For this reason, even if the joystick is returned to the neutral position after the bendable portion is bent in a certain direction, it may happen that the operation force will not be transmitted fully to the bendable portion. In such a case, the bendable portion may not be restored into its substantially linear state, which corresponds to the neutral position of the stick.

In the conventional art, when the bendable portion is bent and then restored into the substantially linear state corresponding to the neutral position, the operator intentionally operates the stick in the direction opposite to that in which it has been slanted. By so doing, the bendable portion can be restored into the linear state corresponding to the neutral position.

Jpn. Pat. Appln. KOKAI Publication No. 5-15486 discloses a control means for detecting the degree to which a bendable portion is bent and controlling the time for which a driving mechanism is operated until the bendable portion is restored into the linear state.

The degree to which the bendable portion is operated in the direction opposite to that in which it has been slanted and the time for which the driving mechanism should be operated, are determined by parameters. The parameters are preset for a control circuit and represent a predetermined extent.

BRIEF SUMMARY OF THE INVENTION

An endoscope according to one aspect of the present invention comprises:

a flexible insertion section which is insertable into a space to be inspected, the insertion section including a bendable portion at a distal end thereof;

a bending mechanism located on a proximal side of the insertion section, the bending mechanism being configured to drive the bendable portion;

a centering control section configured to control the bending mechanism such that the bendable portion is returned to a neutral position where the bendable portion is substantially linear;

a centering instruction input section from which an instruction for controlling the centering control section is input; and a return position adjustment section configured to vary the bend of the bendable portion when the bendable portion is returned to the neutral position, the return position adjustment section operating when the centering control section is operated and determining the bend in accordance with a bending characteristic difference the bendable portion has between bending directions.

When the bendable portion is restored from a bent state, the centering instruction input section is operated to input an instruction supplied to the centering control section. As a result, the centering control section controls the bending mechanism until the bendable portion returns to a neutral position where the bendable portion is substantially linear. By operating the centering control section, the return position adjustment section varies the bend of the bendable portion when the bendable portion is returned to the neutral position. The return position adjustment section determines the bend in accordance with a bending characteristic difference the bendable portion has between bending directions. Accordingly, centering with high precision is enabled for each bending direction.

The return position adjustment section includes: a recognition section configured to recognize a bending characteristic variance the bendable portion may undergo in each bending direction; and a bend-varying section configured to vary the bend the bendable portion should have when the bendable portion is returned to the neutral position, on the basis of a recognition result of the recognition section.

When the bendable portion is restored from a bent state, the recognition section of the return position adjustment section recognizes a bending characteristic variance the bendable portion may undergo in each bending direction. On the basis of a recognition result of the recognition section, the bend-varying section varies the bend the bendable portion should have when it is returned to the neutral position.

The centering instruction input section of the centering control section is connected to a parameter storage section. The parameter storage section stores parameters based on which a centering instruction signal is generated. When the centering instruction input section is operated, it outputs an instruction to generate a centering instruction signal and supplies it to the centering control section on the basis of a centering parameter stored in the parameter storage section.

The operation section includes a remote control. The remote control includes a joystick. The centering instruction input section includes a centering button located near the joystick of the remote controller. The centering button of the centering control section is connected to a parameter storage section. The parameter storage section stores parameters based on which a centering instruction signal is generated. When the centering button is operated, it outputs an instruction to generate a centering instruction signal and supplies it to the centering control section on the basis of a centering parameter stored in the parameter storage section.

The return position adjustment section includes a personal computer detachably attached to the endoscope. The personal computer is connected to the centering control section, and the parameters in the parameter storage section are directly changed by use of the personal computer in such a manner that the bend the bendable portion should have when it is returned to the neutral position is varied in accordance with a bending characteristic variance the bendable portion may undergo in each bending direction. Of the parameters, those parameters corresponding to the directions in which the bendable portion can hardly restore its original shape are increased.

The insertion section includes an internal channel inside, and the recognition section includes a photo-coupler configured to detect whether or not a treatment device is inserted in the internal channel.

The bend-varying section includes two parameter storage sections that store different centering parameters. The centering parameters are data representing how the bendable portion should operate when it is subject to a centering operation after being bent in a given direction. The two parameter storage sections are specifically a first parameter storage section and a second parameter storage section. The bend-varying section further includes a switch section interposed between the centering control section and the two parameter storage sections. The first parameter storage section stores data representing how the bendable portion should operate in each bending direction where the treatment device is not inserted in the internal channel. The second parameter storage section stores data representing how the bendable portion should operate in each bending direction where the treatment device is inserted in the internal channel. The switch section operates on the basis of a recognition result of the photo-coupler and switches the first and second parameter storage sections from one to the other so as to perform a centering operation.

An endoscope according to another aspect of the present invention comprises:

a flexible insertion section which is insertable into a space to be inspected, the insertion section including a bendable portion at a distal end thereof;

a bending mechanism located on a proximal side of the insertion section, the bending mechanism being configured to drive the bendable portion;

a recognition section configured to recognize a bending characteristic variance the bendable portion may undergo in each bending direction; and a bend-varying section configured to vary a bend the bendable portion should have, on the basis of a recognition result of the recognition section.

When the bendable portion is restored from a bent state, the recognition section recognizes a bending characteristic variance the bendable portion may undergo in each bending direction. On the basis of a recognition result of the recognition section, the bend-varying section varies the bend of the bendable portion in such a manner that centering with high precision is enabled for each bending direction.

The recognition section includes a determination section configured to determine whether or not the bending characteristic has varied by detecting whether there is a treatment device channel through which a treatment device is inserted into the insertion section.

Based on the detection of the treatment device channel through which the treatment device is inserted into the insertion section, the determination section determines whether or not the bending characteristic has varied. Centering with high precision is therefore enabled for each bending direction.

The insertion section includes a treatment device channel into which the treatment device is inserted, and the recognition section includes a treatment device detecting section configured to determine whether or not the bending characteristic has varied by detecting a treatment device inserted into the treatment device channel.

With this configuration, the recognition section recognizes a state where a treatment device is inserted in the treatment device channel, a state where an external channel tube is attached to the outer portion of the insertion section, or a state where forceps are inserted through the external channel tube. Based on this recognition, appropriate parameters are determined, a bending characteristic variance is determined, and centering with high precision is enabled for each bending direction.

The bending mechanism includes operating wires used for bending the bendable portion, and a driving motor configured to pull the operating wires. The recognition section includes a determination section configured to make a determination based on the current value of the driving motor.

Whether or not the bending characteristic has been varied is determined by detecting the current value of the driving motor of the bending mechanism. Based on this determination, centering with high precision is enabled for each bending direction.

The bending mechanism includes operating wires used for bending the bendable portion, and a driving motor configured to pull the operating wires. The recognition section includes a determination section configured to make a determination based on the voltage applied to the driving motor.

Whether or not the bending characteristic has been varied is determined by detecting the voltage applied to the driving motor of the bending mechanism. Based on this determination, centering with high precision is enabled for each bending direction.

The bend-varying section includes an addition section configured to add digital signals to control signals used for bending the bendable portion. The digital signals are added on the basis of a recognition result of the recognition section when the bending characteristic the bendable portion has for each bending direction varies.

The insertion section includes an attachment portion to which an external channel for insertion of the treatment device is detachably attached, and the determination section includes an external channel detector used for determining whether or not the external channel is attached to the attachment portion.

The external channel detector includes a contact used for detecting the external channel.

The determination section includes a photo-coupler used for determining whether the treatment device is inserted into the treatment device channel.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5A is a sectional view taken along line VA—VA of FIG. 4B.

FIG. 5B is a sectional view taken along line VB—VB of FIG. 4B.

FIG. 5C is a sectional view taken along line VC—VC of FIG. 5A.

FIG. 6A is a longitudinal sectional view illustrating how the chain-driving sprocket of an electric bending device is assembled in the industrial endoscope apparatus of the first embodiment.

FIG. 6B is a longitudinal sectional view illustrating a coupler between a chain and an operating wire.

FIG. 6C is a longitudinal sectional view illustrating how the chain-driving sprocket for vertical bending is assembled.

FIG. 6D is a longitudinal sectional view illustrating how the chain-driving sprocket for horizontal bending is assembled.

DETAILED DESCRIPTION OF THE INVENTION

Figure 1:
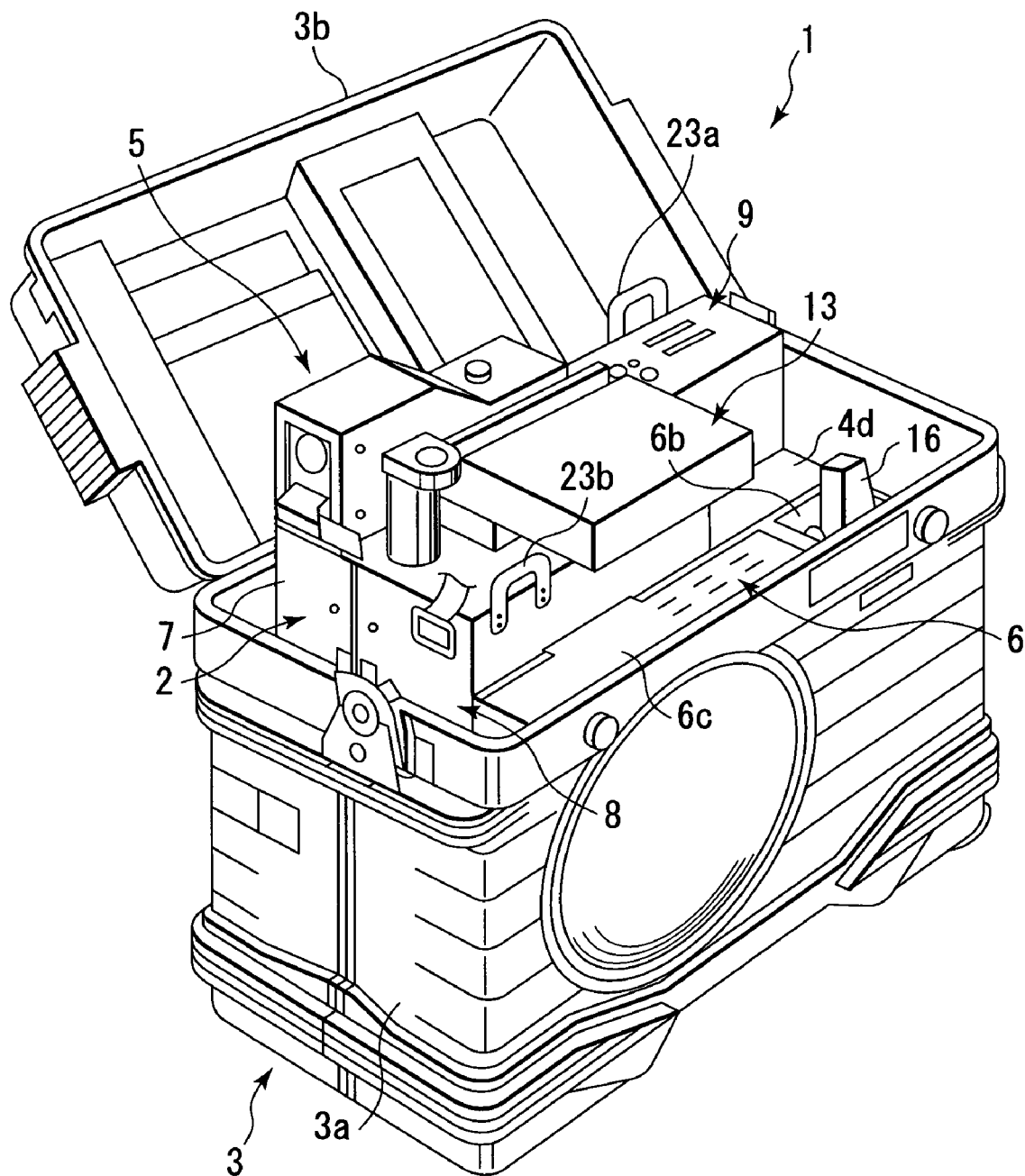
FIG. 1 is a perspective view of the entire industrial endoscope apparatus according to the first embodiment of the present invention, the perspective view illustrating a state where the cover of an endoscope storage case is open.

The first embodiment of the present invention will now be described with reference to FIGS. 1 through 10. FIG. 1 shows an industrial endoscope apparatus 1 of the embodiment. The endoscope apparatus 1 is provided with an assembling unit 2 which integrally assembles the structural elements of an endoscope, and an endoscope storage case 3 in which the assembling unit 2 is removably stored.

Figure 2A:
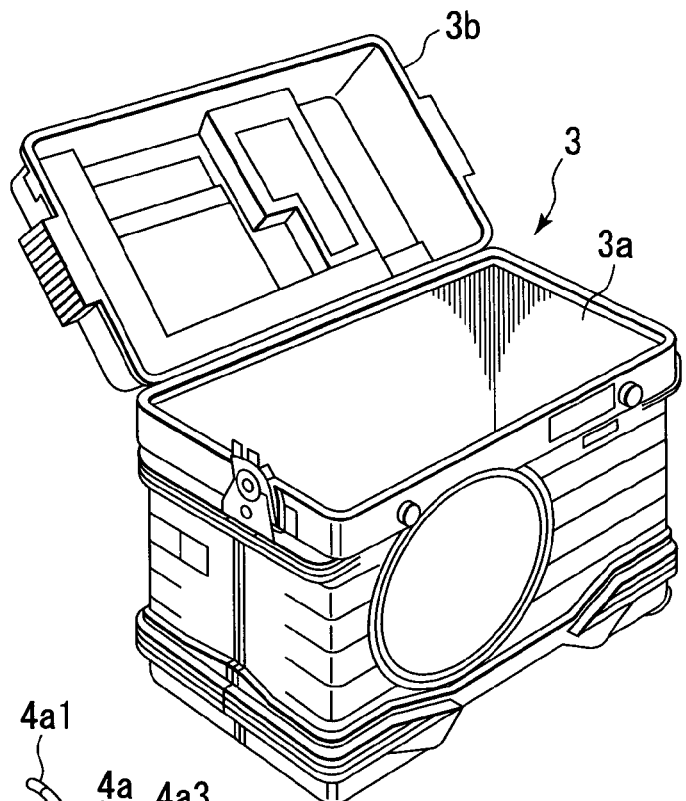
FIG. 2A is a perspective view of the endoscope storage case of the industrial endoscope apparatus of the first embodiment.

As shown in FIG. 2A, the endoscope storage case 3 includes a box-shaped case main body 3a and a cover 3b. The case main body 3a has an open upper section. The open upper section can be closed with the cover 3b. The cover 3b is rotatably coupled to one edge of the open upper section of the case main body 3a by means of a hinge (not shown). FIG. 1 shows the state where the assembling unit 2 is stored in the endoscope storage case 3, with the cover 3b open.

Figure 2B:
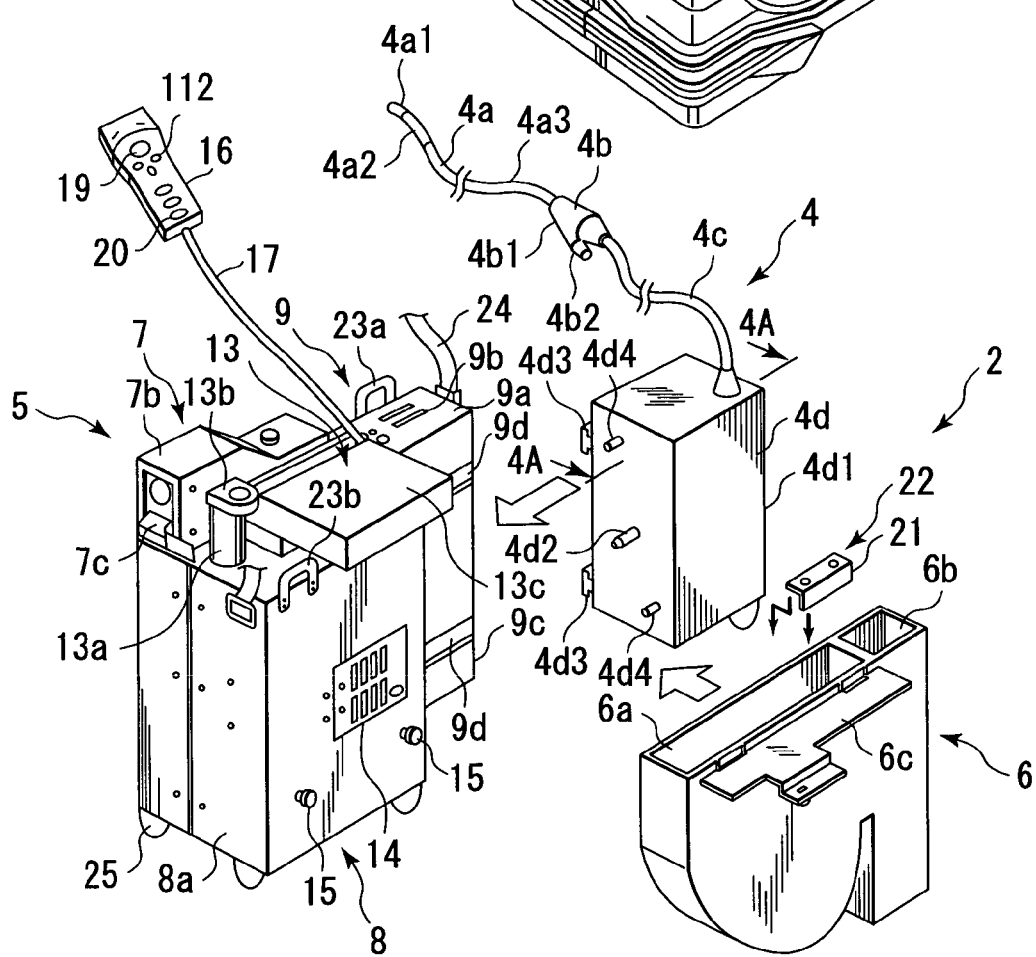
FIG. 2B is an exploded perspective view of an assembling unit of the main body of the endoscope apparatus.

FIG. 2B is an exploded perspective view of the assembling unit 2 of the endoscope apparatus 1. The assembling unit 2 includes a scope section 4, a fixing unit 5 and a storage section 6. The scope section 4, the fixing unit 5 and the storage section 6 are assembled together in a detachable manner.

The scope section 4 includes at least the following: an elongated flexible insertion section 4a which is to be inserted into a space to be inspected; an intermediate coupler 4b; a universal cable 4c; and a base unit 4d (i.e., a section for driving the insertion section). The insertion section 4a is located at the distal end and is provided with the following: a head 4a1 in which an observation optical system, an illuminating optical system, etc. are incorporated; a bendable portion 4a2 which can be operated remotely; and an elongated flexible tube 4a3. The bendable portion 4a2 is located between the head 4a1 and the flexible tube 4a3.

Figure 3:
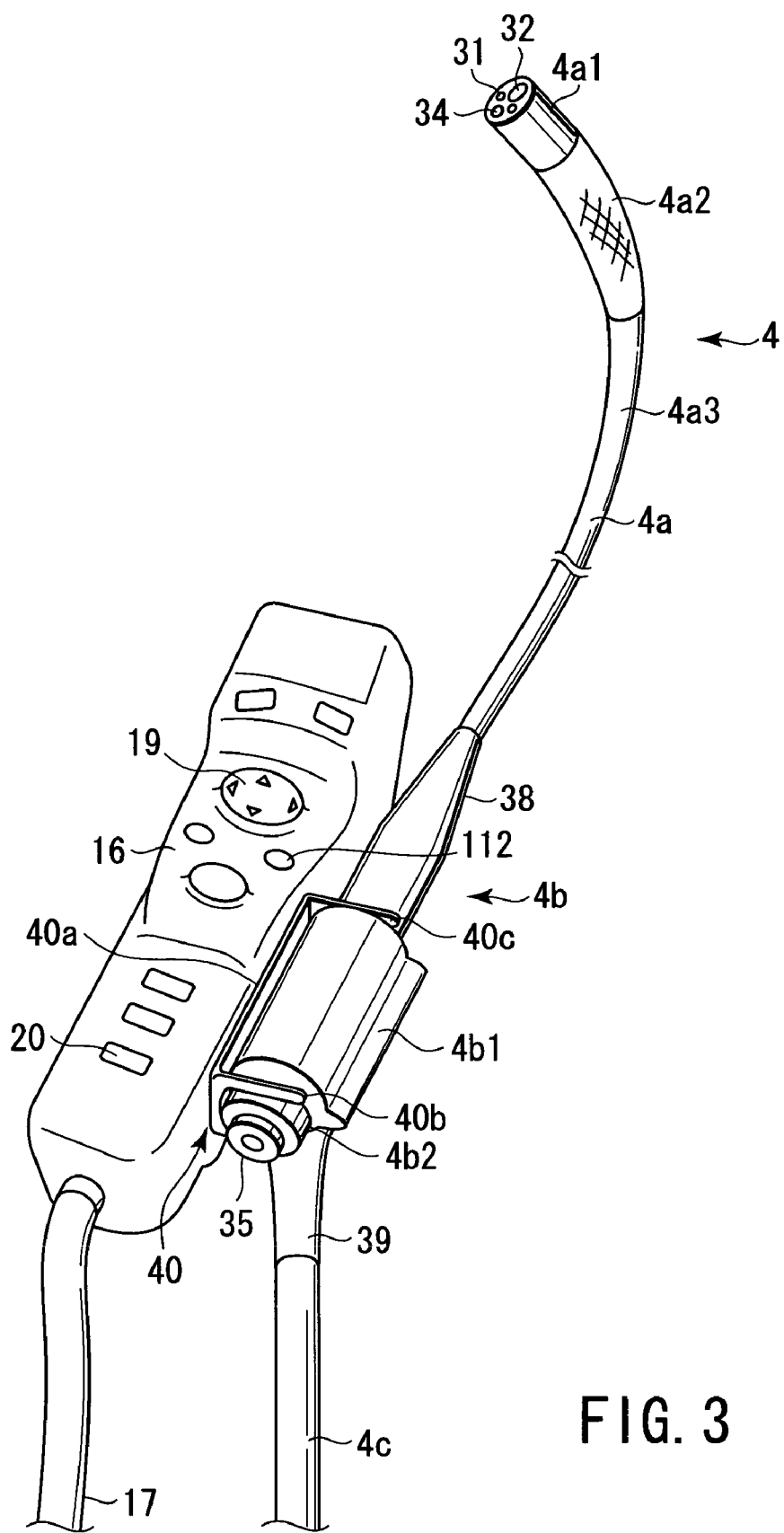
FIG. 3 is a perspective view of an intermediate coupler of the scope section of the industrial endoscope apparatus of the first embodiment.

As shown in FIG. 3, an illumination window 31 of the illuminating optical system, an observation window 32 of the observation optical system, a distal-end opening 34 of an internal channel (a treatment device passage) 33 (shown in FIG. 8) of the insertion section 4a, etc. are open in the distal end face of the head 4a1.

Figure 8:
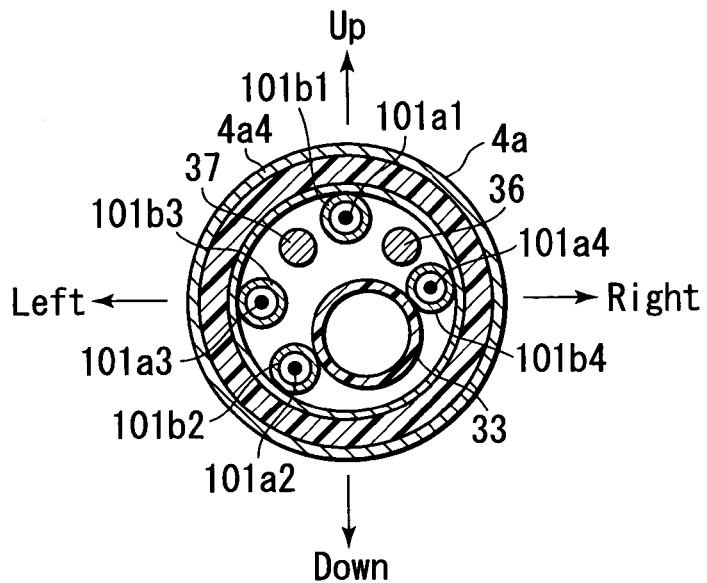
FIG. 8 is a cross sectional view illustrating the internal structure of the insertion section of the industrial endoscope apparatus of the first embodiment.

As shown in FIG. 8, a light guide 36, a signal line 37, and a plurality of angle wires (operating wires) 101a1 to 101a4 (which are four in number in the present embodiment) are arranged inside the insertion section 4a. The light guide 36 is an optical passage through which light is transmitted to the observation window 31. The signal line 37 is connected, for example, to a CCD of the observation optical system. The four angle wires 101a1 to 101a4 are used for bending the bendable portion 4a2.

In the present embodiment, angle wires 101a1 and 101a2 are used for vertical bending. The remaining angle wires 101a3 and 101a4 are used for horizontal bending. The bendable portion 4a2 of the insertion section 4a is vertically bent by use of the two vertically-bending angle wires 101a1 and 101a2, and is horizontally bent by use of the two horizontally-bending angle wires 101a3 and 101a4. Using these four wires, the bendable portion 4a2 is bent upward, downward, rightward, leftward, or in any direction desired.

The angle wires 101a1 to 101a4, which are arranged in the internal region of the tube of the insertion section 4a, are inserted in angle coils 101b1 to 101b4, for protection. The outer circumferential surface of the insertion section 4a is covered with an outer blade 4a4.

As shown in FIG. 3, the distal end of the intermediate coupler 4b is coupled to the proximal end of the flexible tube 4a3 of the insertion section 4a. The intermediate coupler 4b comprises a grip portion 4b1. The grip portion 4b1 is taken hold of by the operator. At the rear end of the grip portion 4b1, a channel port 4b2 and a coupler to the distal end of the universal cable 4c are juxtaposed. The channel port 4b2 has a forceps opening 35 (an opening at the proximal end) that communicates with an internal channel 33. The internal channel 33 extends through the insertion section 4a in the axial direction thereof. The coupler to the universal cable 4c is slanted relative to the axial direction of the insertion section 4a.

The light guide 36, signal line 37 and four angle wires 101a1 to 101a4 extending from the insertion section 4a are inserted into the interior of the universal cable 4c.

The intermediate coupler 4b has an insertion section-protecting rubber portion 38. The insertion section-protecting rubber portion 38 serves to prevent the insertion section 4a from being bent acutely. The intermediate coupler 4b has a universal cable-protecting rubber portion 39. The universal cable-protecting rubber portion 39 serves to prevent the universal cable 4c from being bent acutely.

Figures 4A, 4B:
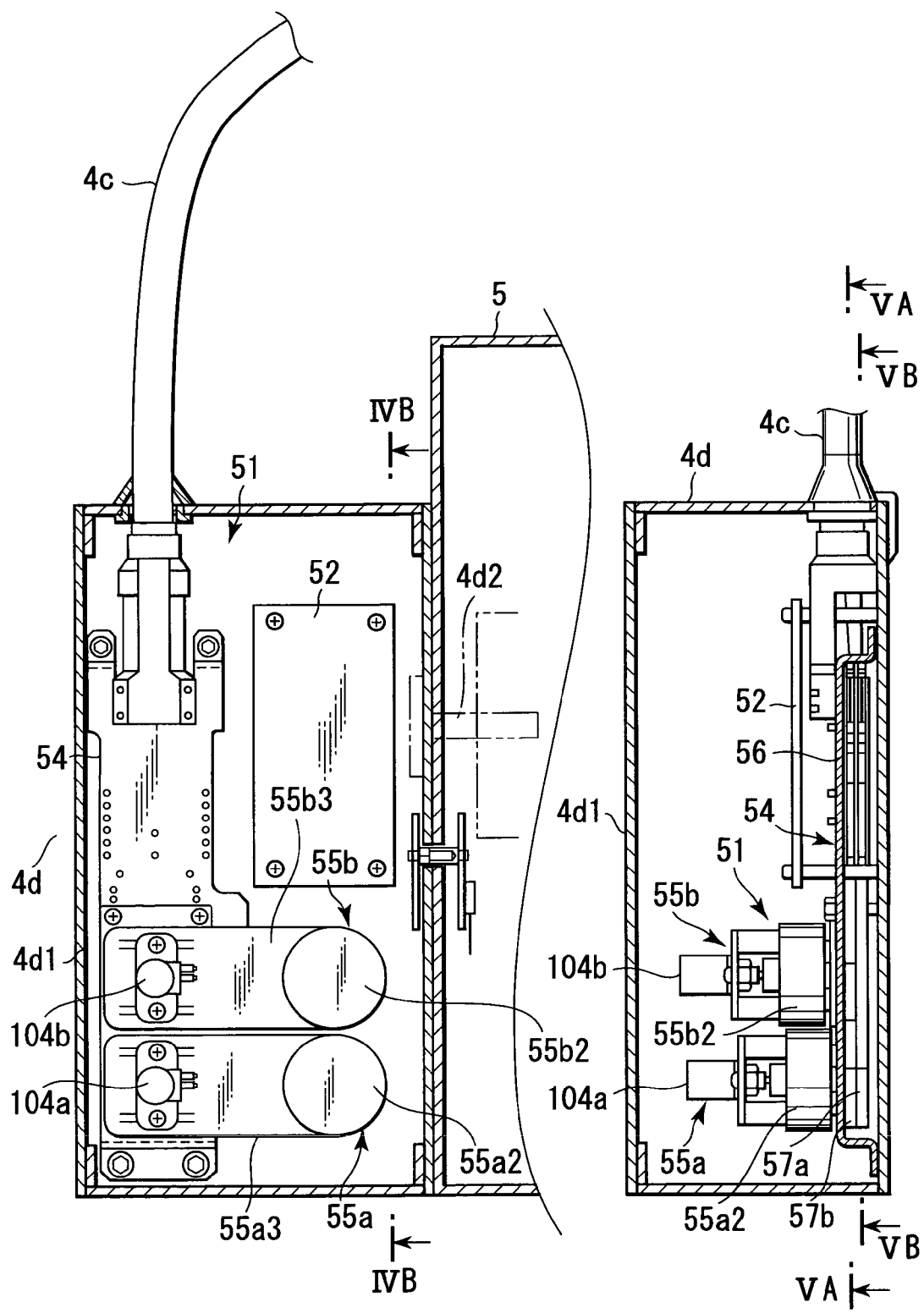
FIG. 4A is a longitudinal sectional view showing the internal structure of the scope section of the industrial endoscope apparatus of the first embodiment.
FIG. 4B is a sectional view taken along line IVB—IVB of FIG. 4A.

As shown in FIG. 4A, the proximal end of the universal cable 4c is coupled to a base unit 4d. The base unit 4d comprises a unit case 4d1, an electric bending device (a bending mechanism) 51, an electric bending controller 52 for controlling the electric bending device 51, a camera control unit (CCU) 53 (shown in FIG. 7), etc. These structural components are contained in the unit case 4d1.

The electric bending device 51 comprises a pulling force transmission mechanism unit 54, and two motor units 55a and 55b for vertical and horizontal bending operations. The two motor units 55a and 55b are located under the pulling force transmission mechanism unit 54.

Motor unit 55a comprises an output shaft 55a1, a motor section 55a2 serving as a driving source for generating a driving force, a decelerating gear section 55a3, and a potentiometer 104a. Likewise, motor unit 55b comprises an output shaft 55b1, a motor section 55b2 serving as a driving source for generating a driving force, a decelerating gear section 55b3, and a potentiometer 104b. The decelerating gear sections 55a3 and 55b3 are made of gear trains (e.g., spur gear trains) for transmitting the driving forces of the motor sections 55a2 and 55b2 to the output shafts 55a 1 and 55b1. The potentiometers 104a and 104b detect rotations of the output shafts 55a 1 and 55b1. The potentiometers 104a and 104b are arranged in parallel to the motor sections 55a2 and 55b2, respectively, with the corresponding decelerating gear sections 55a3 and 55b3 being located therebetween.

The pulling force transmission mechanism unit 54 has an upper end attached to the upper end portion of the unit case 4d1. The proximal end of the universal cable 4c is coupled to the upper end portion of the pulling force transmission mechanism unit 54. The two motor units 55a and 55b are installed in the lower region of the unit case 4d.

As shown in FIGS. 6A and 6B, the pulling force transmission mechanism unit 54 comprises a unit case 56. Two pulling force transmission mechanisms 57a and 57b, which correspond to the two bending directions of the bendable portion 4a2, are provided inside the unit case 56. One (57a) of the two pulling force transmission mechanisms 57a and 57b is shown in FIG. 5B. As shown in FIG. 6A, pulling force transmission mechanism 57a includes: a sprocket 58a fixed to the output shaft 55a1 of the vertically-bending motor unit 55a; and a chain 59a engaged with the sprocket 58a. The output shaft 55a1 of the motor unit 55a is of a double shaft type. In other words, the motor unit 55a has two output shafts extending in the opposite directions. The sprocket 58a is attached to one of the output shafts 55a1, and the potentiometer 104a is provided at the other output shaft.

The proximal ends of two angle wires 101a1 and. 101a2 are coupled to the two ends of the chain 59a by means of coupling members 60a1 and 60a2, respectively. With this structure, the pulling force transmission mechanism 57a shown in FIG. 5B interlocks with the motor unit 55a, thereby providing a vertically-bending driving mechanism 51a.

When the vertically-bending motor unit 55a rotates the sprocket 58a, the chain 59a and the coupling members 60a1 and 60a2 are driven, and the vertically-bending angle wires 101a1 and 101a2 are pulled or loosened.

The other pulling force transmission mechanism 57b is shown in FIG. 5A. As shown in FIG. 6A, pulling force transmission mechanism 57b includes: a sprocket 58b fixed to the output shaft 55b1 of the horizontally-bending motor unit 55b; and a chain 59b engaged with the sprocket 58b. The output shaft 55b1 of the motor unit 55b is of a double shaft type. In other words, the motor unit 55b has two output shafts extending in the opposite directions. The sprocket 58b is attached to one of the output shafts 55b1, and the potentiometer 104b is provided at the other output shaft.

The proximal ends of two angle wires 101a3 and 101a4 are coupled to the two ends of the chain 59b by means of coupling members 60a3 and 60a4, respectively. With this structure, the pulling force transmission mechanism 57b shown in FIG. 5A interlocks with the motor unit 55b, thereby providing a horizontally-bending driving mechanism 51b.

When the horizontally-bending motor unit 55b rotates the sprocket 58b, the chain 59b and the coupling members 60a3 and 60a4 are driven, and the horizontally-bending angle wires 101a3 and 101a4 are pulled or loosened.

With the structure described above, the vertically-bending motor unit 55a of the electric bending mechanism 51 pulls the two vertically-bending angle wires 101a1 and 101a2. Likewise, the horizontally-bending motor unit 55b pulls the two horizontally-bending angle wires 101a3 and 101a4. Hence, the bendable portion 4a2 can be bent in a vertical direction, in a horizontal direction or in any direction combined. When the bendable portion 4a2 is bent, the potentiometers 104a and 104b sense the rotated positions of the sprockets 58a and 58b. On the basis of sensing signals supplied from the potentiometers 104a and 104b, the electric bending controller 52 controls the positions of the angle wires 101a1 to 101a4, thereby controlling the operation of bending the bendable portion 4a2.

Figure 7:
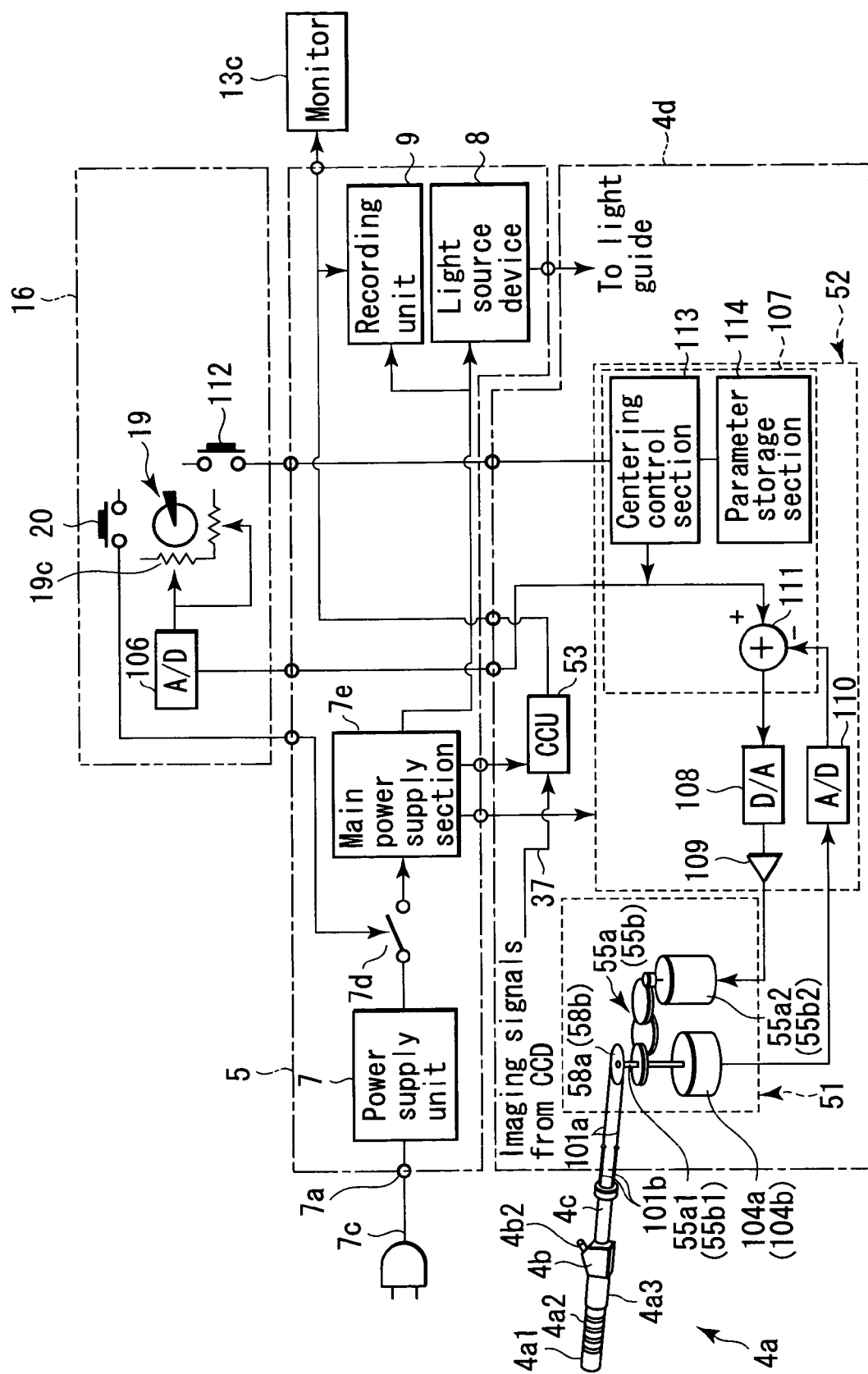
FIG. 7 is a schematic diagram illustrating the entire control circuit of the industrial endoscope apparatus of the first embodiment.

As shown in FIG. 7, the proximal end of the signal line 37 is connected to the camera control unit 53. The distal end of the signal line 37 is connected to the CCD located inside the insertion section 4a. Image data representing endoscopic observation images obtained by the CCD are converted into electric signals, and these electric signals are supplied to the camera control unit 53 through the signal line 37.

As shown in FIG. 2B, a light guide connector 4d2 is projected from an end surface of the unit case 4d1 of the base unit 4d. The proximal end of a light guide (not shown) extending from the universal cable 4c is coupled to the light guide connector 4d2.

A pair of attachment/detachment guides 4d3, namely, upper and lower attachment/detachment guides, are provided on another side surface of the unit case 4d1 of the base unit 4d. The guides 4d3 extend substantially in the horizontal direction. When the base unit 4d and the fixing unit 5 are coupled, the guides 4d3 guide the movement of the base unit 4d. A plurality of fixing members 4d4 are projected from the above-mentioned end surface of the unit case 4d1. When the base unit 4d and the fixing unit 5 are coupled, the fixing members 4d4 come into detachable engagement with receiving portions (not shown) of the fixing unit 5. In this manner, the base unit 4d is fixed to the fixing unit 5.

The fixing unit 5 includes a power supply unit 7, a light source device 8 and a recording unit 9. The power supply unit 7 is provided with a power supply connector 7a (FIG. 7) and a power supply cover 7b. A power supply cable 7c is connected to the power supply connector 7a. The power supply unit 7 is connected to a main power supply section 7e through a switch 7d.

The recording unit 9 has a front panel 9a in which a plurality of insertion slits 9b are formed. Recording mediums, such as memory cards, are inserted through the slits 9b. The recording unit 9 has a side plate 9c in which a pair of U-shaped guide grooves 9d are formed. The guide grooves extend in a substantially horizontal direction. The attachment/detachment guides 4d3 of the base unit 4d are brought into detachable engagement with the guide grooves 9d. The guide grooves 9d serve to guide the movement of the base unit 4d.

As shown in FIG. 2B, the light source device 8 comprises an outer cover 8a. Although not shown, a lamp box provided with a light source lamp; a relay board; a lamp line board; an EL connector board; an IL switch; a ballast; a fan; etc. are contained in the outer cover 8a.

The outer cover 8a of the light source device 8 is provided with a receiving portion (not shown) formed in the surface with which the base unit 4d of the scope section 4 is brought into contact. The light guide connector 4d2 of the base unit 4d is brought into detachable engagement with that receiving portion.

To couple the light source device 8 of the fixing unit 5 to the base unit 4d of the scope section 4, the attachment/detachment guides 4d3 of the base unit 4d of the scope section 4 are inserted in the guide grooves 9d of the recording unit 9. In this state, the attachment/detachment guides 4d3 are slid along the guide grooves 9d until the base unit 4d of the scope section 4 is detachably coupled to the light source device 8 of the fixing unit 5. At the time, the light guide connector 4d2 of the base unit 4d comes into detachable engagement with the receiving portion (not shown) of the light source device 8. In addition, the fixing members 4d4 of a first connection mechanism 10 come into engagement with the receiving portion (not shown) of the fixing unit 5. In this manner, the light source device 8 of the fixing unit 5 and the base unit 4d of the scope section 4 are coupled together.

When the fixing unit 5 and the base unit 4d of the scope section 4 are coupled together, the main power supply section 7e is electrically connected to the electric bending controller 52 and the camera control unit 53 through electric contacts. Then, an LCD monitor 13c is connected to the camera control unit 53 through the electric contacts between the base unit 4d and the fixing unit 5. Therefore, the endoscopic observation images obtained by the CCD of the scope section 4 are displayed on the LCD monitor 13c.

Although not shown, a remote control connector, a BNC connector and a display device 13 are provided on the upper surface of the outer cover 8a of the light source device 8. The display device 13 comprises an LCD monitor 13c, for example. This LCD monitor 13c is coupled to the top portion of a cylindrical monopod 13a by means of a hinge mechanism 13b. The hinge mechanism 13b enables the LCD monitor 13c to be opened or closed.

As shown in FIG. 2B, a lamp replacement window 14 is formed in a side wall of the outer cover 8a of the light source device 8. A plurality of attachment pins 15 are projected from that side wall, for attaching the storage section 6.

The interior region of the storage section 6 is divided into a plurality of regions. In the case of the present embodiment, it is divided into the following two: a wide scope storage box 6a (i.e., an insertion section storage box); and a narrow remote control storage region 6b (i.e., a region in which a cable or the like is stored). In the scope storage box 6a, the insertion section 4a of the scope section 4, the intermediate coupler 4b and the universal cable 4c are stored in the bundled state. The storage section 6 is provided with a storage box cover 6c, with which the open section of the scope storage box 6a is closed or opened.

A remote control 16 (an input section) and a flexible cable 17 are stored in the remote control storage section 6b. The base unit 4d of the scope section 4 is operated by use of the remote control 16. One end of the cable 17 is connected to the remote control 16. A connector (not shown) is coupled to the other end of the cable 17. This connector is detachably connected to the remote control connector of the fixing unit 5.

The storage section 6 has an attachment surface, which is to be attached to the fixing unit 5. The attachment surface has pin insertion holes (not shown) at positions corresponding to the attachment pins 15 of the light source device 8. When the attachment pins 15 of the light source device 8 are inserted into the pin insertion holes of the storage section 6, the storage section 6 is detachably coupled to the side surface of the outer cover 8a of the light source device 8.

The storage section 6 is provided with a scope storage box push member 21, which is shaped substantially like "L". When the storage section 6 is coupled to the side surface of the outer cover 8a of the storage section 6, the push member 21 is fixed to the fixing unit 5 by means of screws.

The endoscope apparatus 1 of the present embodiment is provided with two handles 23a and 23b and one shoulder belt 24, for placing the assembling case 2 into the endoscope storage case 3 or for taking it out of the case 3. One (23a) of the handles is provided on the upper surface of the recording unit 9 of the fixing unit 5, while the other handle 23b is provided on the upper surface of the outer cover 8a of the light source device 8. One end of the shoulder belt 24 is connected to the upper surface of the recording unit of the fixing unit 5, while the other end is connected to the upper surface of the outer cover 8a of the light source device 8. The assembling unit 2 has a plurality of rubber legs 25 attached to the bottom.

As shown in FIG. 3, a fixing member 40 is fixed to one side of the remote control 16. The fixing member 40 enables detachable coupling of the intermediate coupler 4b. The fixing member 40 includes a base plate 40a, and two engagement portions 40b and 40c which are shaped substantially like "U". The base plate 40a is fixed to one side of the remote control 16. The engagement portions 40b and 40c are located at the respective ends of the base plate 40a and are substantially perpendicular to the lengthwise direction of the base plate 40a. When the grip portion 4b1 of the intermediate coupler 4b is inserted between the engagement portions 40b and 40c located at the respective ends of the fixing member 40, the intermediate coupler 4b comes into detachable engagement with one side of the remote control 16.

The remote control 16 includes at least the following: a joystick 19; a power button 20; and a centering button 112 (e.g., a centering instruction input means). The joystick 19 is an instruction input means for remotely bending the bendable portion 4a2 of the scope section 4 in the vertical and horizontal directions. The power button 20 is connected to the switch 7d of the power supply unit 7.

Figure 9A:
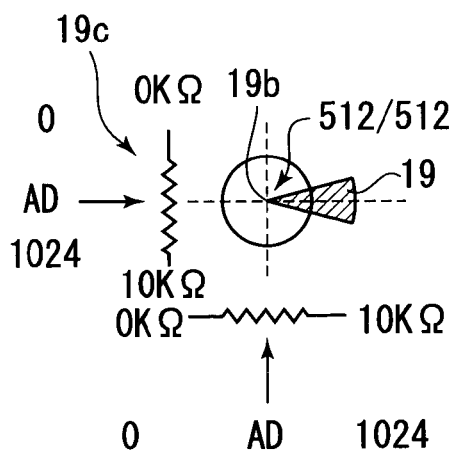
FIG. 9A is an illustration showing how the bending mechanism of the industrial endoscope apparatus of the first embodiment operates.
Figure 9B:
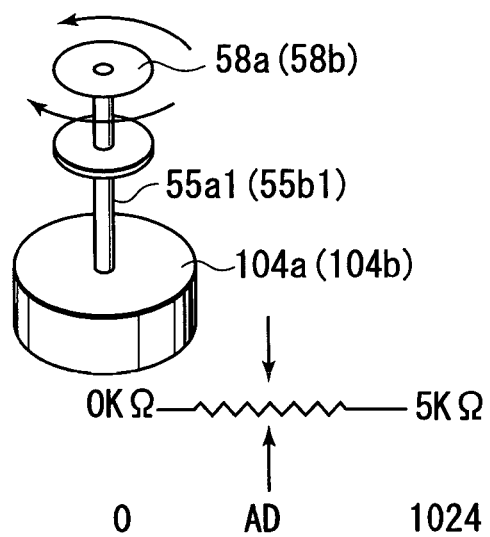
FIG. 9B is an illustration showing how a potentiometer operates.

As shown in FIG. 9A, the joystick 19 has a proximal end serving as a pivotal support point 19, and is pivotally supported. The remote control 16 includes a variable resistor 19c and an A/D conversion section 106. The resistance value of the variable resistor 19c changes in accordance with the slanted direction and angle of the joystick 19. The A/D conversion section 106 converts an analog voltage, which is obtained in accordance with the resistance value of the variable resistance 19c, into a digital signal.

The A/D conversion section 106 of the remote control 16 is electrically connected to the electric bending controller 52 of the fixing unit 5. A bending instruction signal, which is a digital signal obtained at the A/D conversion section 106, is supplied to the electric bending controller 52.

The electric bending controller 52 includes a microcomputer 107, a D/A converter 108, an amplifier 109, and an A/D conversion section 110 used for a potentiometer 110. The microcomputer 107 is electrically connected to the A/D conversion section 106 of the remote control 16 and generates a digital driving signal in response to a bending instruction signal supplied from the remote control 16. The digital driving signal output from the microcomputer 107 is supplied to the D/A converter 108, by which it is converted into an analog driving signal. The output terminal of the D/A converter 108 is connected to the motor sections 55a2 and 55b2 through the amplifier 109. The amplifier 109 amplifies the analog driving signal obtained by the D/A converter 108, and the amplified signal is supplied to the motor sections 55a2 and 55b2.

The microcomputer 107 includes a CPU, a ROM (which stores a program), a RAM (which can store a program), a differential operation section 111, and an A/D conversion section 110 for potentiometers. The input terminal of the A/D conversion section 110 is connected to the potentiometers 104a and 104b, while the output terminal of the A/D conversion section 110 is connected to the differential operation section 110. The A/D conversion section 110 converts analog resistance values, which represent the rotated positions of the potentiometers 104a and 104b, into digital signals. An output signal from the A/D conversion section 110 is supplied to the differential operation section 111. The differential operation section 111 subtracts the bending instruction signal of the A/D conversion section 106 of the remote control 16 from the rotation signals the potentiometers 104a and 104b sense with respect to the sprockets 58a and 58b. The resultant subtracted signals are used for feedback control.

The microcomputer 107 includes a centering control section 113 and a parameter storage section 114. The centering button 112 of the remote control 16 and the parameter storage section 114 are connected to the centering control section 113. A parameter stored in the parameter storage section 114 represents how much the bendable portion should operate temporarily in response to an instruction supplied from the centering button 112. To be more specific, the parameter represents how much the electric bending controller 52 should rotate the electric sprockets 58a and 58b. The rotations of the sprockets are determined based on the rotations of the output shafts 55a1 and 55b1 of the potentiometers 104a and 104b. The signals the microcomputer 107 actually uses are digital signals obtained by dividing the overall resistance of the potentiometers 104a and 104b by a predetermined unit value. In response to an instruction supplied from the centering button 112, the centering control section 113 generates a centering instruction by use of a centering parameter stored in the parameter storage section 114.

Figure 10:
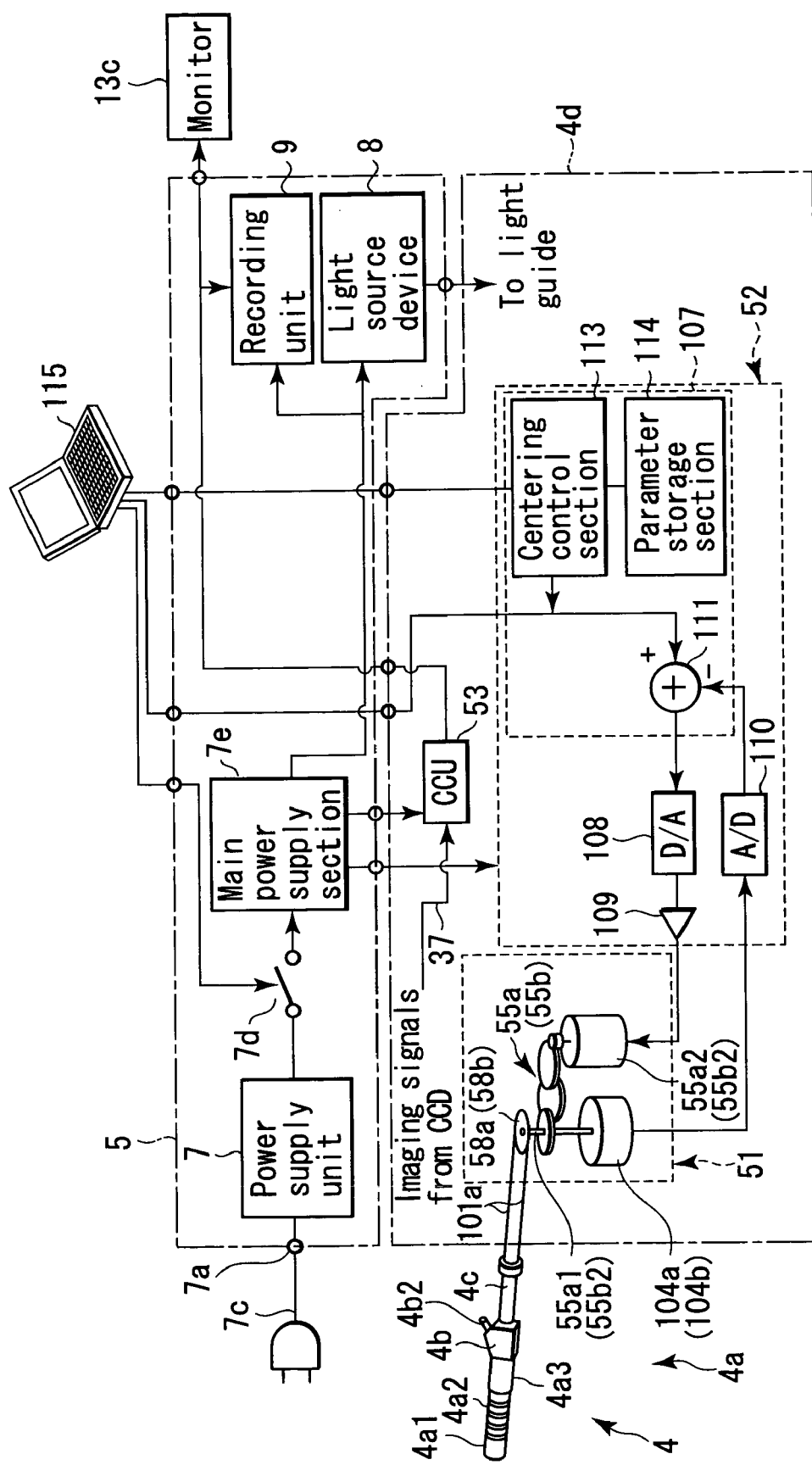
FIG. 10 is a schematic diagram showing how a personal computer is connected to a centering control section in the industrial endoscope apparatus of the first embodiment.

As shown in FIG. 10, the endoscope apparatus 1 of the present embodiment is provided with a personal computer 115 in place of the remote control 16 described above. The personal computer 115 is detachably attached to the fixing unit 5 and serves as a return position adjusting means. The personal computer 115 is connected to the centering control section 113 of the microcomputer 107. The personal computer 115 changes parameters of the parameter storage section 114 directly. With the parameters being changed, the degree to which the bendable portion is operated in the direction opposite to that in which it has been bent, can be controlled in accordance with the bending characteristic corresponding to each direction. To be more specific, when the bendable portion is bent in a desired direction by a desired angle and is then returned to the neutral position, the parameter corresponding to a direction in which the bendable portion cannot be easily returned is increased in accordance with the bending characteristic the bendable portion has in that direction.

A description will now be given of the operation of the above configuration. When the endoscope apparatus 1 of the present invention is carried, the scope section 4, the fixing unit 5 and the storage section 6 shown in FIG. 2B are assembled together to form the assembling unit 2. This assembling unit 2 is stored in the endoscope storage case 3 shown in FIG. 2A. As shown in FIG. 1, the assembling unit 2-is stored in the endoscope storage case 3 and is then covered with the cover 3b. In this state, the endoscope apparatus 1 is carried to a place which is in the vicinity of an object to be inspected.

At the inspection place, the cover 3b of the endoscope storage 3 is opened, as shown in FIG. 1. With the storage box cover 6c kept open, the insertion section 4a of the scope section 4, the intermediate coupler 4b and the universal cable 4c are taken out of the scope storage box 6a. In addition, the remote control 16 and the cable 17 are taken out of the remote control storage region 6b. In this state, the insertion section 4a of the scope section 4 is inserted into a space to be inspected, and the space is subject to endoscopic inspection.

In the endoscopic inspection, the bendable portion 4a2 of the scope section 4 is operated as described below by use of the joystick 19 of the remote control 16. In the initial state, the bendable portion 4a2 of the scope section 4 of the present embodiment is not bent; the bendable portion 4a2 is held at the neutral position where its entirety is substantially linear (i.e., it is in the non-bent state where the bending angle of the bendable portion 4a2 is zero). At the time, the joystick 19 of the remote control 16 stands upright, and the chains 59a and 59b of the two pulling force transmission mechanisms 57a and 57b are neither pulled nor loosened.

To bend the bendable portion 4a2 upward, the operator moves the joystick 19 of the remote control 16 upward. In response to this, an instruction for upward movement is supplied to the A/D conversion section 106 of the remote control 16, for conversion into a digital signal. This digital signal passes through the fixing unit 5 and is then transmitted to the electric bending controller 52.

In the electric bending controller 52, the microcomputer 107 checks the values of the potentiometers 104a and 104b and supplies data on them to the A/D conversion section 110. After being converted into digital signals, the values of the potentiometers 104a and 104b are supplied to the differential operation section 111. The differential operation section 111 calculates the difference components between the rotations of the sprockets 58a and 58b sensed by the potentiometers 104a and 104b and the bending instruction signals supplied from the A/D conversion section 106 of the remote control 16. Based on this calculation, an instruction is output for bending the bendable portion 4a2 upward from the linear state is output.

To be more specific, the A/D conversion section 106 converts the resistance of the variable resistor 19c of the joystick 19b into a digital signal having a 1024-gradation value in the range from "0" to "1023." Likewise, the A/D conversion section 110 converts the resistance values of the potentiometers 104a and 104b into digital signals having 1024-gradation values in the range from "0" to "1023."

When the rotational position of the sprocket 58a for vertical bending is neutral, the A/D conversion section 110 outputs median value "512." Likewise, when the joystick 19 is at the neutral position, the A/D conversion section 106 outputs median value "512." Value "0" corresponds to the maximally upward direction, and value "1023" corresponds to the maximally downward direction. Similarly, the rotational position of the sprocket 58b for horizontal bending and the inclination angle of the joystick 19 are determined in such a manner that value "0" denotes the maximally leftward direction and value "1023" denotes the maximally rightward direction.

When an instruction for upward bending is input from the joystick 19, the A/D conversion section 106 of the remote control 16 supplies value "0" to the electric bending controller 52. At the time, the value of the A/D conversion section 110 is "512." Therefore, the differential operation section 111 supplies the D/A converter 108 with an instruction corresponding to a differential amount of (0–512). The instruction is supplied through the amplifier 109 to the motor section 55a2 of the motor unit 55a. The differential operation section 111, the D/A converter 108, the amplifier 109, the motor section 55a2 for vertical bending, the potentiometer 104a and the A/D conversion section 110 continue to operate until the value of the A/D conversion section 110 becomes "0."

When the operator moves his or her hand off the joystick 19, the joystick 19 returns to the neutral position of itself. At the time, the A/D conversion section 106 of the remote control 16 outputs signal "512." In this case, therefore, the differential operation section 111 subtracts signal "0" (which is an output of the A/D conversion section 110) from signal "512" (which is an output of the A/D conversion section 106 of the remote control 16). Since the subtraction performed then is (512−0), an instruction for moving back to the neutral position is output. When the A/D conversion section 110 outputs "512", the motor section 55a2 is stopped, and the bending operation is thereby stopped.

Even after the sprocket 58a returns to the neutral position, the bendable portion 4a2 may not completely move back to the neutral position. This is because the force corresponding to the position of the sprocket 58a is not fully transmitted to the distal end of the bendable portion 4a2, due to the frictional resistance between the angle wire 101a and the angle coil 101b. That is, the bendable portion 4a2 may be bent slightly upward then. Although the operator has moved the joystick to the neutral position by then, he or she naturally expects that the bendable portion 4a2 should be at the neutral position, which is not actually the case.

The centering function is utilized for coping with this case. The centering function is enabled by depressing the centering button 112 of the remote control 16. In response to the depression of the centering button 112, a centering instruction is supplied to the centering control section 113, and a centering operation is executed using a parameter stored in the parameter storage section 114. A detailed description will be given as to how this centering operation is executed.

Where the bendable portion 4a2 is bent upward before the joystick 19 is returned to the neutral position, the bendable portion 4a2 may be bent slightly upward even after the joystick 19 is moved back to the neutral position. In this case, therefore, the centering button 112 of the remote control 16 is depressed to provide a centering instruction, based on which the bendable portion 4a2 is bent downward to a certain degree. If the operation of bending the bendable portion 4a2 is excessive, the bendable portion 4a2 will be in the downwardly bent state. In other words, the degree to which the bendable portion 4a2 is bent downward based on the centering instruction should be appropriate. This bending degree is determined by a parameter.

The operation of bending the bendable portion 4a2 downward based on the centering operation is started in the state where the bendable portion 4a2 is bent slightly upward. In this state, the sprocket 58a is slightly rotated in the direction corresponding to downward bending, and is then moved to the neutral position. Assuming that the parameter is "30", the potentiometer 104a is moved from the position corresponding to "512" to the position corresponding "512+30", and is then immediately moved back to the position corresponding to "512."

The angle wires 101a1 and 101a2 are momentarily operated in such a way as to bend the bendable portion 4a2 downward. In other words, the angle wire 101a2 for downward bending is pulled, and immediately thereafter the angle wire 101a1 for upward bending is pulled to move the sprocket 58a to the neutral position. By operating the angle wires 101a1 and 101a2 in this manner, the bendable portion 4a2 is momentarily bent downward and is then bent upward. Although the bendable portion 4a2 is bent downward, it is soon bent upward.

The upward bending operation described above is intended to move the bendable portion 4a2 from "542" to "512", and the bendable portion 4a2 is not operated sufficiently. In addition, the angle at which the bendable portion 4a2 remains is of a very small value. Moreover, the downward bending operation of the bendable portion 4a2 is a slight operation in practice by reason of the friction between the angle wire 101a and the angle coil 101b. Therefore, there may be a case where the bendable portion 4a2 is only restored to the neutral state from the slightly bent state.

The structural components inside the insertion section 4a are not arranged uniformly in the radial direction. As shown in FIG. 8, they are arranged in an eccentric fashion. In the example shown in FIG. 8, the channel tube of the internal channel 33, which is soft and has a low restoring force, is located in the lower right region of the cross section of the insertion section 4a. It should be noted here that "having a low restoring force" means that the tube cannot be easily restored into its original state after it is bent. Hence, the tube prevents the bendable portion 4a2 from being restored into the original state even after the joystick 19 of the remote control 16 is moved back to the neutral position. In other words, in the example shown in FIG. 8, the bendable portion 4a2 does not easily return to the neutral position after it is bent rightward or downward, and it returns to the neutral position with comparative ease after it is bent leftward or upward. This is attributable to the difference in the radius of curvature between the case where the bendable portion 4a2 is bent rightward or downward and the case where it is bent leftward or upward. Where the bendable portion 4a2 is bent rightward or downward, the radius of curvature of the channel tube of the internal channel 33 is of a small value, compared to the case where the bendable portion 4a2 is bent leftward or upward. The bendable portion 4a2 is hard to return to the neutral position, accordingly.

As can be understood from the above, the parameters corresponding to the four directions must be different. If they are of the same value, the rightward or downward centering does not work satisfactorily.

In the present embodiment, therefore, the personal computer 115 is connected in the manner shown in FIG. 10, and changes the values of the parameters of the parameter storage section 114 on the basis of the directions in which the bendable portion 4a2 can be bent. For example, the parameters corresponding to the directions in which the bendable portion 4a2 does not easily return are increased, such as "upward 30", "downward 40", "rightward 40" and "leftward 30."

When the bendable portion 4a2 is bent rightward or leftward, an instruction input at the time of centering is determined in such a manner that the operation of the bendable portion 4a2 is slightly greater in the leftward or upward direction. Although the instruction signal transmitted to the distal end of the bendable portion 4a2 may be attenuated to some extent, sufficient centering of the bendable portion 4a2 is ensured. Hence, the centering operation can be executed with high accuracy without reference to the characteristics of the channel tube of the internal channel 33.

The structure described above is advantageous in the following points: The endoscope apparatus 1 of the present embodiment is provided with the parameter storage section 114 configured to store variable parameters and the personal computer 115 configured to change the values of the parameters of the parameter storage section 114. The personal computer 115 is connected in the manner shown in FIG. 10 in place of using the remote control 16, and the values of the parameters stored in the parameter storage section 114 are changed directly in accordance with the four directions in which the bendable portion 4a2 can be bent. With this structure, the bendable portion 4a2 can return accurately to the neutral position and becomes substantially linear after it is bent in any direction. In this manner, optimal centering is ensured without reference to the bending direction of the bendable portion 4a2.

Figure 11:
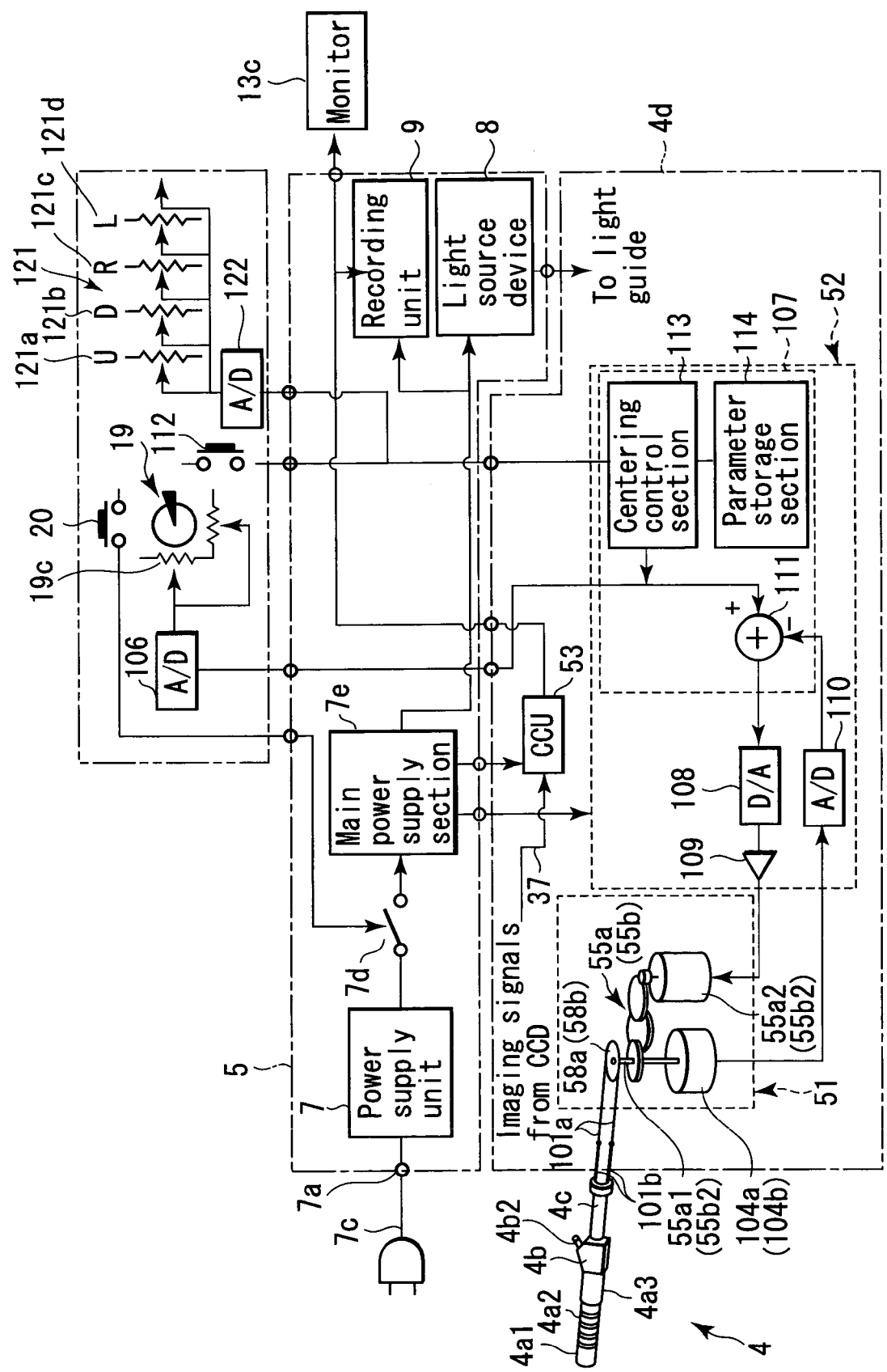
FIG. 11 is a schematic diagram illustrating the entire control circuit of the industrial endoscope apparatus of the second embodiment.

FIG. 11 shows the second embodiment of the present invention. The second embodiment differs from the first embodiment (shown in FIGS. 1 through 10) in that the endoscope apparatus 1 is modified as describe below.

As shown in FIG. 11, the remote control 16 of the second embodiment is provided with a centering parameter-changing volume 121. This volume 121 serves as a return position adjusting means and controls the degree to which the bendable portion 4a2 is returned to the neutral position in the direction opposite to that in which it has been bent, in accordance with the bending characteristic corresponding to each direction. The volume 121 includes a volume 121a for upward centering, a volume 121b for downward centering, a volume 121c for rightward centering and a volume 121d for leftward centering.

Like other analog signals, the analog signals output from these volumes 121a–121d are converted into digital signals by a centering A/D conversion section 122. After this conversion, the signals from the volumes 121a–121d are sent to the centering control section 113 of the microcomputer 107 by way of the fixing unit 5, so that the parameters of the parameter storage section 114 can be directly changed for control.

In the second embodiment, the volumes 121a–121d of the centering parameter-changing volume 121 of the remote control 16 are operated to directly change the parameters of the parameter storage section 114. As in the first embodiment, when the centering control section 113 operates, the degree to which the bendable portion 4a2 is returned to the neutral position can be optimally determined in accordance with the bending characteristic corresponding to each direction. Hence, the bendable portion 4a2 can return accurately to the neutral position and becomes substantially linear after it is bent in any direction, and optimal centering is ensured at all times.

The second embodiment may be provided with a means for detecting the slanted direction and angle of the joystick 19. Where such a detection means is provided, the volumes 121a–121d of the centering parameter-changing volume 121 of the remote control 16 are automatically changed in accordance with results of detection of the detection means.

The second embodiment may employ a touch panel monitor 13c in place of the structure that changes the volumes 121a to 121d of the centering parameter-changing volume 121 of the remote control 16. Where such a touch panel monitor 13c is employed, the values of the parameters of the parameter storage section 114 can be changed on the software basis by operating the menu displayed on the monitor 13c.

Figure 12:
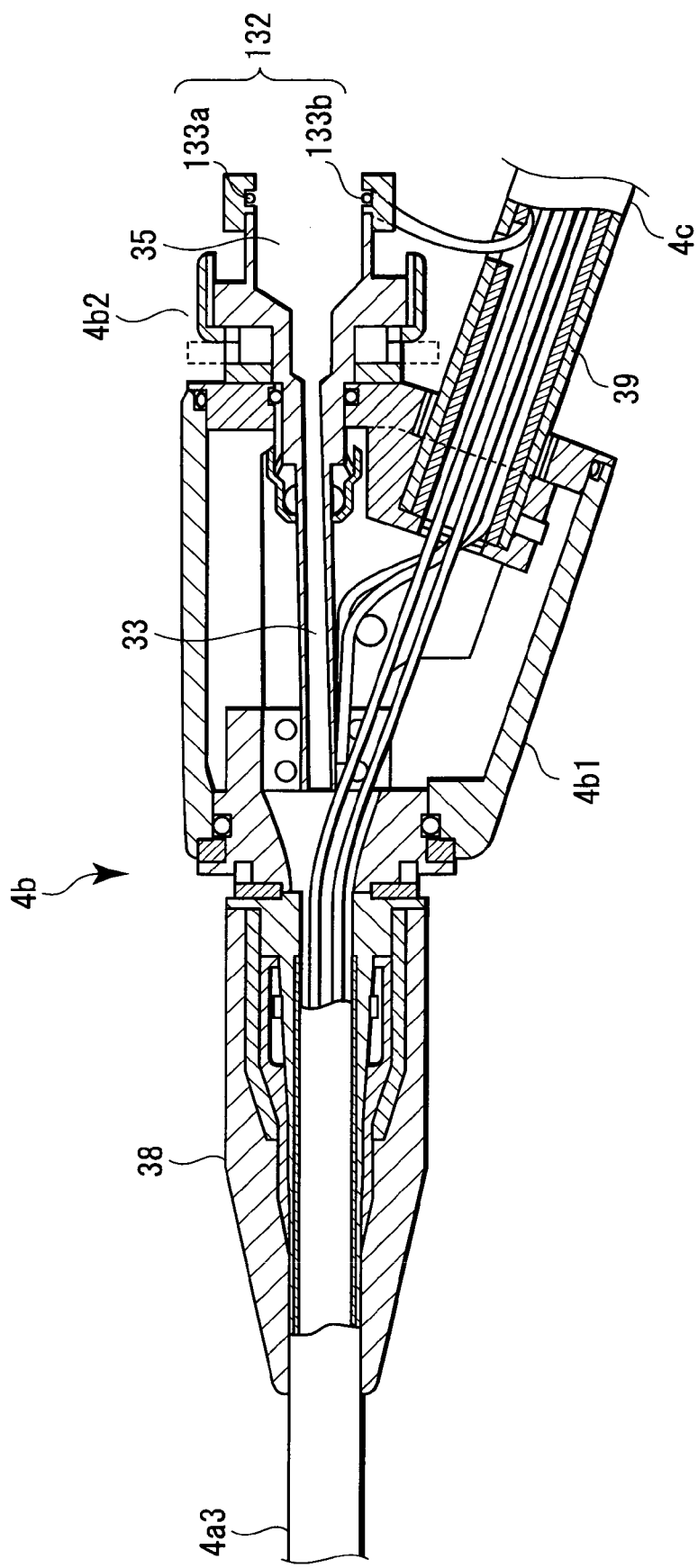
FIG. 12 is a longitudinal sectional view showing an intermediate coupler of the scope section of an industrial endoscope apparatus according to the third embodiment of the present invention.

FIG. 12 through FIGS. 15A–15D show the third embodiment of the present invention. The third embodiment is obtained by modifying the endoscope apparatus 1 of the first embodiment (shown in FIGS. 1 through 10) as follows:

As shown in FIG. 12, the third embodiment employs a recognition means 132 for recognizing whether forceps 131 (FIG. 14) are present in the channel port 4b2 of the intermediate coupler of the scope section 4. The recognition means 132 includes photo-couplers 133a and 133b.

Figure 13:
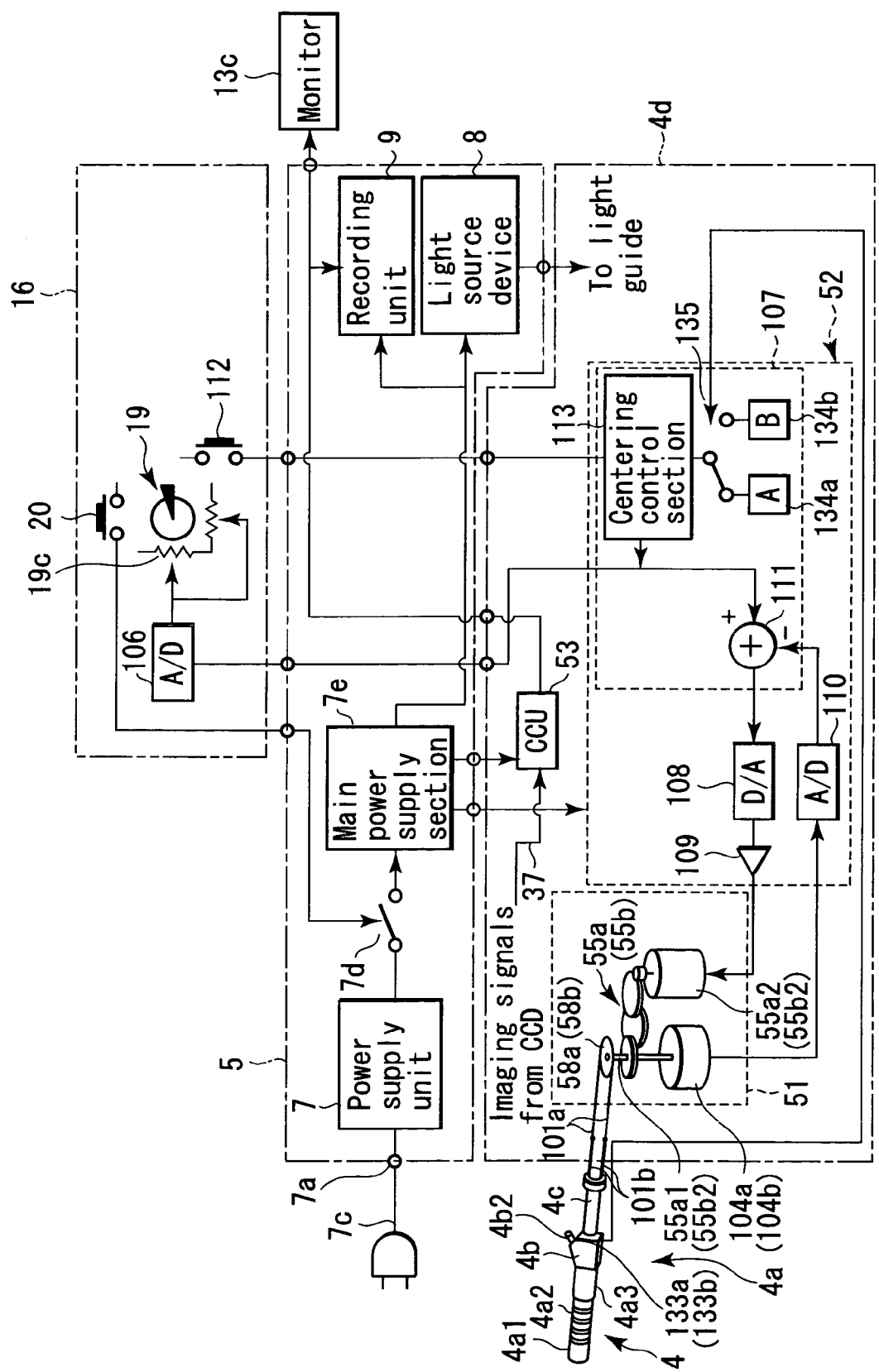
FIG. 13 is a schematic diagram illustrating the entire control circuit of the industrial endoscope apparatus of the third embodiment.
Figure 14:
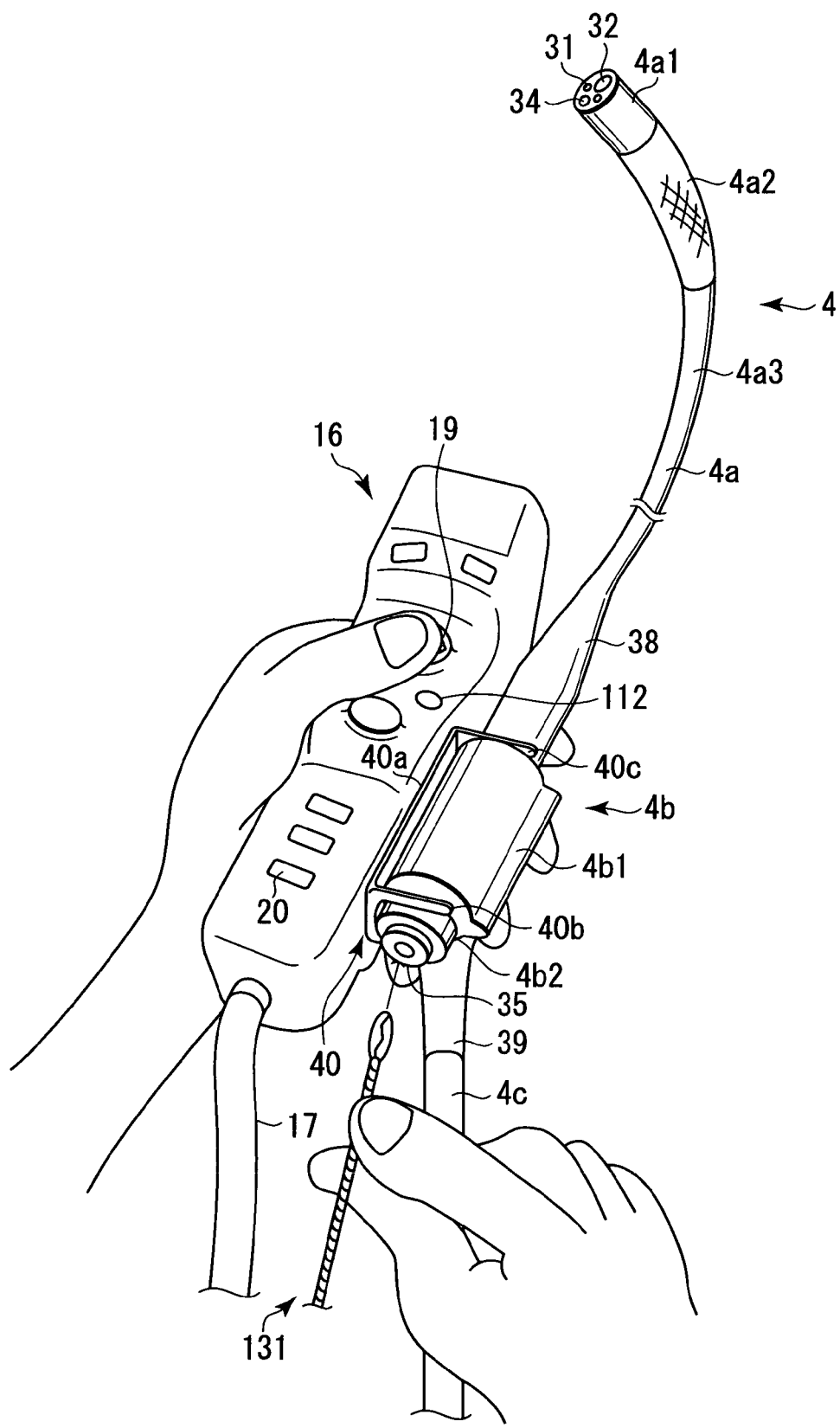
FIG. 14 is a perspective view illustrating how forceps are inserted into the forceps inlet of the intermediate coupler in the industrial endoscope apparatus of the third embodiment.

In addition, as shown in FIG. 13, the micro-computer 107 of the electric bending controller 52 is provided with a bend control means for controlling the bend which the bendable portion 4a2 should have when it is returned to the neutral position on the basis of the recognition results of the recognition means 132. The bend control means includes two parameter storage sections 134a and 134b and a switch 135. Each of the two parameter storage sections 134a and 134b stores centering parameters corresponding to upward, downward, rightward and leftward directions and used for performing a centering operation after the bendable portion 4a2 is bent in the upward, downward, rightward and leftward directions. However, the centering parameters stored in parameter storage section 134a differ from those stored in parameter storage section 134b. For example, parameter storage section 134a (referred to as "A" parameter storage section) stores "30", "40", "40" and "30" as data corresponding to upward, downward, rightward and leftward directions, respectively, and used for performing a centering operation when the forceps 131 are not inserted in the internal channel 33.

On the other hand, parameter storage section 134b (referred to as "B" parameter storage section) stores "10", "20", "20" and "10" as data corresponding to upward, downward, rightward and leftward directions, respectively, and used for performing a centering operation when the forceps 131 are inserted in the internal channel 33.

The switch 135 is located between the centering control section 113 and the two parameter storage sections 134a, 134b. The photo-couplers 133a and 133b are connected to the switch 135. On the basis of the recognition results from the photo-couplers 133a and 133b, the switch 135 performs switching between the "A" parameter storage section 133a and the "B" parameter storage section 133b. In this manner, these parameter storage sections are selectively used on the basis of the recognition results of the photo-couplers 133a and 133b, when a centering operation is performed.

A description will now be given of the operation of the third embodiment described above. When a centering operation is performed after the bendable portion 4a2 is bent in the upward, downward, rightward or leftward direction, it is necessary to take into account not only the eccentric state of the structural components shown in FIG. 8 but also the presence or absence of the forceps 131 inserted into the internal channel 33 shown in FIG. 14.

In the case where the forceps 131 are inserted into the internal channel 33 in the state shown in FIG. 8, this has to taken into account when the bendable portion 4a2 is bent in every direction. In other words, the bending operation has to be controlled not only in the rightward and downward directions but also in every direction. Let us consider that the forceps 131 have a high degree of rigidity. In this case, the rigidity of the forceps enables the joystick 19 to be easily restored into the neutral state after the bending operation of the forceps 131. If the parameters stored in the parameter storage section 114 and coping with the case where the forceps 131 are inserted into the internal channel 33 are applied, the centering operation will be excessively performed.

Figure 15B:
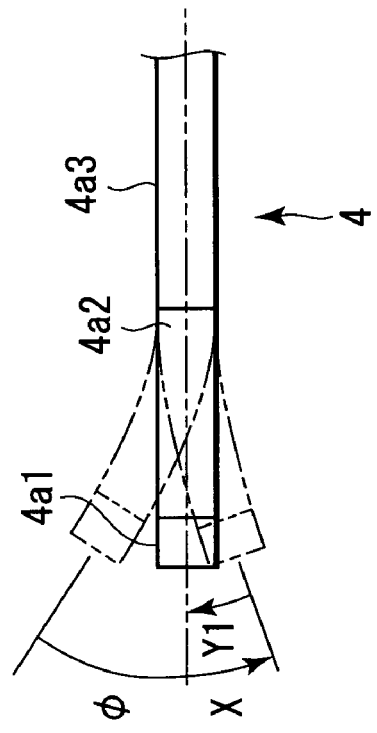
FIG. 15B is an illustration showing how a centering operation of the bendable portion is performed in the case of FIG. 15A.
Figure 15D:
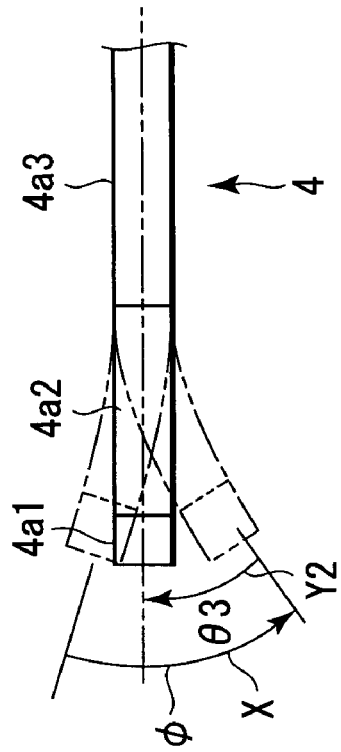
FIG. 15D is an illustration showing how a centering operation of the bendable portion is performed in the case of FIG. 15C.
Figure 15A:
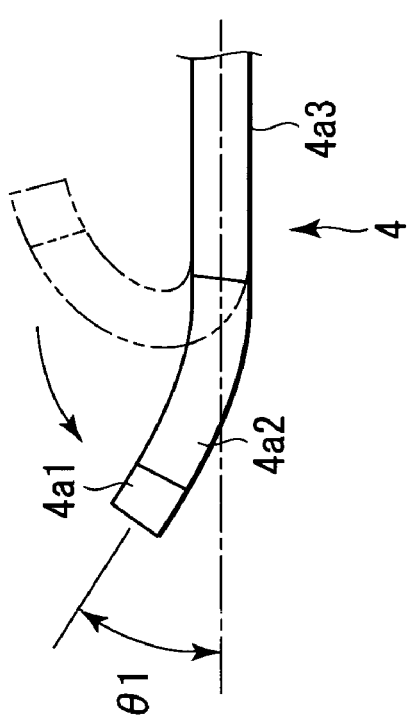
FIG. 15A is an illustration showing how the bendable portion of the industrial endoscope apparatus of the third embodiment is restored from a bent state when the forceps are not inserted in the channel.

FIG. 15A shows how the bendable portion 4a2 will be when it is bent without inserting the forceps 131 into the internal channel 33 and then the joystick 19 is returned to the neutral position. FIG. 15B illustrates how a centering operation is performed from the state shown in FIG. 15A.

In the case where the joystick 19 is operated until the bendable portion 4a2 is bent upward to the position indicated by the imaginary lines in FIG. 15A, and then the joystick 19 is moved back to the neutral position, the bendable portion 4a2 will stop in the state where it is slightly bent in the upward direction. The angle the bendable portion 4a2 forms then is $\theta 1$.

If the centering button 112 of the remote control 16 is thereafter depressed for a centering operation, the operation for moving the bendable portion 4a2 back to the neutral position is a combination of the following two bending operations: the downward bending operation of angle $\phi$ indicated by arrow X in FIG. 15B; and the upward bending operation indicated by arrow Y1 and moving back the bendable portion 4a2. That is, the bendable portion 4a2 is returned to the neutral position in the manner indicated by the solid lines in FIG. 15B.

Figure 15C:
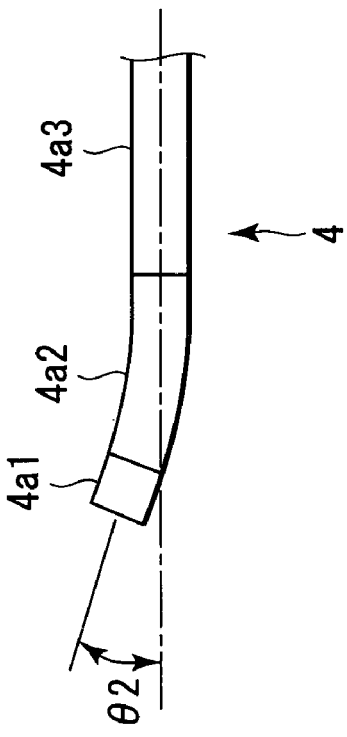
FIG. 15C is an illustration showing how the bendable portion is restored from a bent state when the forceps are inserted in the channel.

FIG. 15C shows how the bendable portion 4a2 will be when it is bent, with the forceps 131 inserted into the internal channel 33, and then the joystick 19 is returned to the neutral position. FIG. 15D illustrates how a centering operation is performed from the state shown in FIG. 15C.

Where the joystick 19 is operated until the bendable portion 4a2 is bent upward, and then the joystick 19 is moved back to the neutral position, the bendable portion 4a2 is hardly bent by reason of the resiliency of the forceps 131, as shown in FIG. 15C. The angle the bendable portion 4a2 forms then is, for example, $\theta 2$ ($\theta 2<\theta 1$). When, in this state, the centering button 112 of the remote control 16 is depressed for a centering operation, the downward bending operation of angle $\phi$ indicated by arrow X in FIG. 15D is first performed. It should be noted that the position corresponding to angle X is close to the neutral position in this case. Therefore, although angle $\phi$ is the same as that of the case shown in FIG. 15B, angle $\theta 3$ is greater than that of the case shown in FIG. 15B. In other words, after the bendable portion 4a2 is bent downward, it must be moved greatly in the upward direction, as indicated by arrow Y2 in FIG. 15D. That means that the bendable portion 4a2 has to be greatly moved upward from the end position of angle X.

Although the operator merely wants to move the bendable portion 4a2 shown in FIG. 15C from the position corresponding to $\theta 2$ to the neutral position, the centering operation shown in FIG. 15D may result in an excessive movement of the bendable portion 4a2. That is, the bendable portion 4a2 moves by angle $\theta 3$, as indicated by arrow Y2, and this results in a movement unnecessary for inspection.

The third embodiment therefore employs the photo-couplers 133a and 133b to detect whether or not the forceps 131 are inserted in the internal channel 33, and switches between the "A" parameter storage section 133a and the "B" parameter storage section 133b by means of the switch 135. Where the forceps 131 are not present in the internal channel 33, the switch 135 connects the "A" parameter storage section 133a to the centering control section 113. On the other hand, where the forceps 131 are present in the internal channel 33, the switch 135 connects the "B" parameter storage section 133b to the centering control section 113 to use parameters of small values.

As described above, in the third embodiment, the photo-couplers 133a and 133b detects whether or not the forceps 131 are present in the internal channel 33, and the switch 135 makes switching between the "A" parameter storage section 133a and the "B" parameter storage section 133b on the basis of the results of detection. With this feature, the bendable portion 4a2 can be returned to the neutral position with an appropriate force. After being bent in a desired direction, the bendable portion 4a2 can be returned to the neutral position where it is substantially linear. Hence, highly precise centering effects are attained.

In the third embodiment, the switch 135 makes switching between the "A" parameter storage section 133a and the "B" parameter storage section 133b. In place of this structure, the centering parameter-changing volume 121 of the second embodiment (FIG. 11) may be used to directly change the values of the parameters of the parameter storage section 114.

In addition, the recognition section may be an electrode that is set in an electrically conductive state when the forceps 131 are inserted. In this case as well, the switch 135 makes switching between the "A" parameter storage section 133a and the "B" parameter storage section 133b.

The electrode need not be exposed to the outside; it may be replaced with a non-contact switch that is turned on or off in response to the insertion-of the forceps 131.

In connection with the third embodiment, reference was made to the case where the "A" parameter storage section 133a and the "B" parameter storage section 133b are switched from one to the other. However, the present invention is not limited to this structure. For example, the recognition means may identify a plurality of types of forceps, and parameter storage sections 114 may be provided in such a manner that they are equal in number to the types the recognition means identifies. In this case, switch 135 selects one of the parameter storage sections 114, and a centering operation is based on the parameters of the selected parameter storage section 114.

Figure 16:
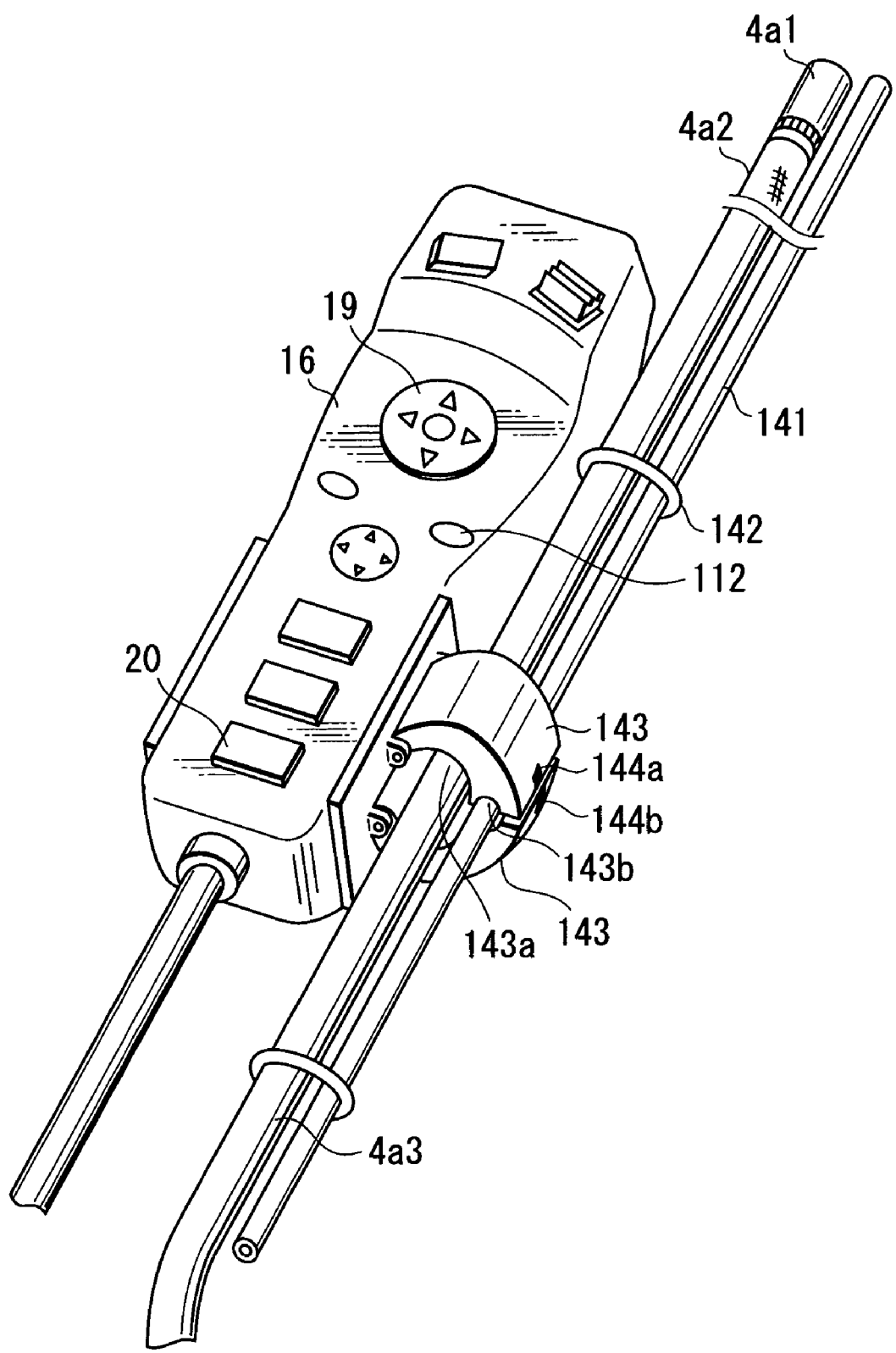
FIG. 16 is a perspective view showing how a scope section provided with an external channel is coupled to a remote control in the industrial endoscope apparatus of the fourth embodiment of the present invention.

FIG. 16 shows the fourth embodiment of the present invention. The fourth embodiment differs from the first embodiment (FIGS. 1 through 10) in that the endoscope apparatus 1 is modified as follows:

In the first embodiment, the insertion section 4a contains the internal channel 33. In the fourth embodiment, the internal channel 33 is replaced with an external channel 141, as shown in FIG. 16. This external channel 141 is attached to the insertion section 4a and bundled together with it by means of a bundling member, such as a tape, an O ring, a binder, or the like. That is, the external channel is used as a side channel of the endoscope.

A pair of clamping members 143 are provided on one side of the remote control 16. The clamping members 143 can be opened or closed and are capable of clamping the insertion section 4a of the scope section 4. Each clamping member 143 has two concave portions on the inner surface thereof. One is a large concave portion 143a configured to hold the insertion section 4a of the scope section 4, and the other is a small concave portion 143b configured to hold the external channel 141.

The clamping members 143 have contacts 144a and 144b, for the detection of the external channel 141. The contacts 144a and 144b are located near the small concave portions 143b. When the contacts 144a and 144b are electrically connected to each other, it is determined that the clamping members 143 clamp and hold the external channel 141. In response to this determination, the switch 135 shown in FIG. 13 performs switching.

In the fourth embodiment, the contacts 144a and 144b of the clamping members 143 are used for determining whether or not the external channel 141 is used, and the "A" parameter storage section 133a and the "B" parameter storage section 133b are switched from one to the other on the basis of the determination. Hence, it is possible to appropriately determine how the bendable portion 4a2 should be bent when it is returned to the neutral position. When the bendable portion 4a2 is bent in a certain direction and is then returned to the neutral position, the presence of the external channel 141 does not become a problem. That is, the bendable portion 4a2 can be reliably returned to the neutral position with high accuracy and becomes substantially linear without reference to the external channel 141. Hence, highly precise centering effects are attained.

In place of the contacts 144a and 144b, the photo-couplers 133a and 133b shown in FIG. 12 may be used for determining whether the external channel 141 has been attached.

Figure 17:
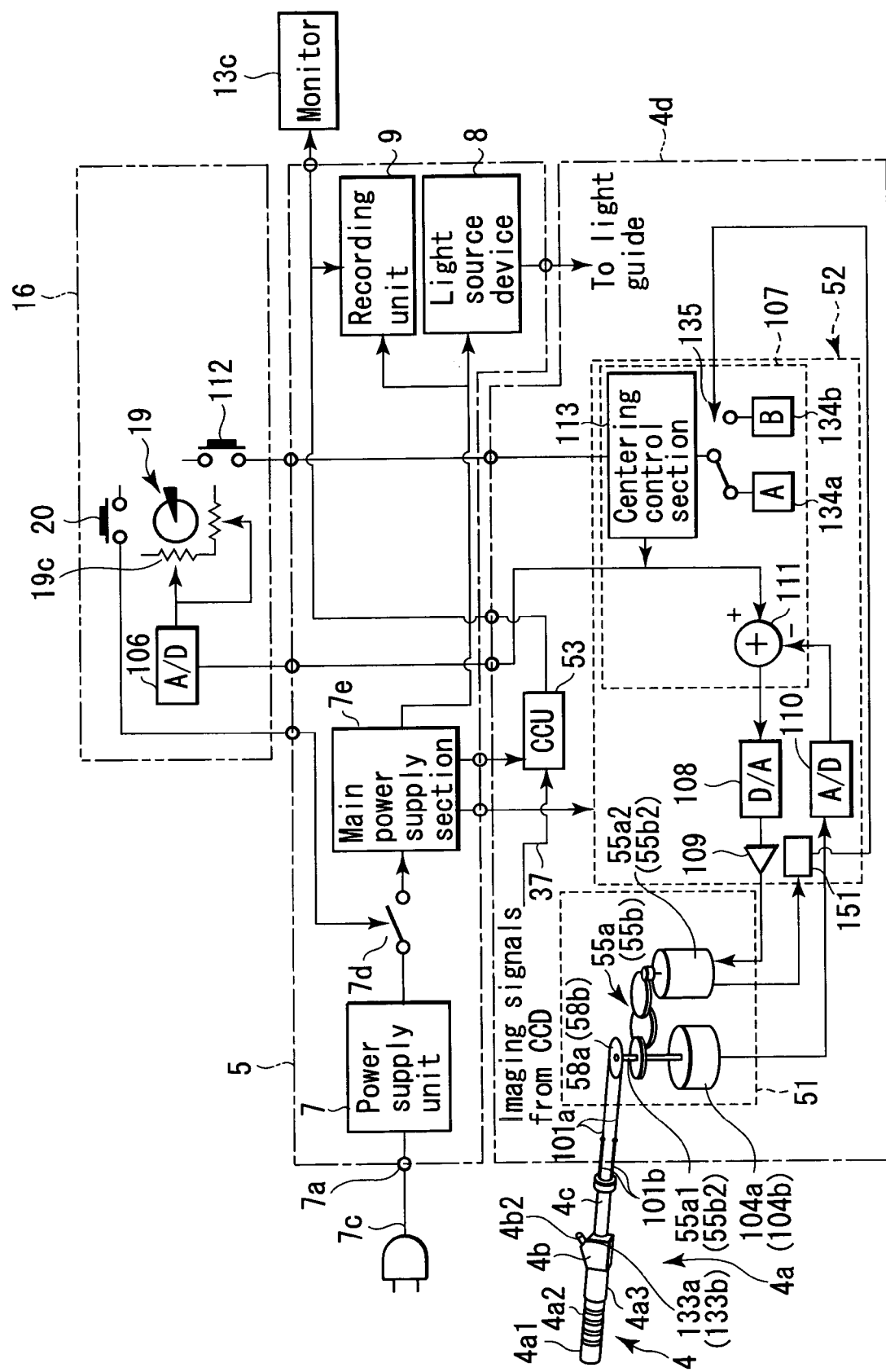
FIG. 17 is a schematic diagram illustrating the entire control circuit of an industrial endoscope apparatus according to the fifth embodiment of the present invention.

FIG. 17 shows the fifth embodiment of the present invention. The fifth embodiment differs from the third embodiment (shown in FIG. 12 to FIGS. 15A–15D) in that the endoscope apparatus 1 is modified as follows:

The fifth embodiment is provided with a current sensing section 151 for sensing the currents supplied to the motor sections 55a2 and 55b2 of the electric bending device 51. The current sensing section 151 is connected to a switch 135 similar to that employed in the third embodiment. When the current value sensed by the current sensing section 151 exceeds a predetermined setting value, the switch 135 switches between the two parameter storage sections 134a and 134b.

In general, the bending characteristic of the bendable portion 4a2 is determined by a variety of factors. These factors include not only the eccentric state of the structural components and the presence or absence of forceps but also a winding or looping movement of the insertion section 4a. To be more specific, if the insertion section 4a winds or loops, the friction between the angle wires 101a and the angle coils 101b increases. In accordance with this increase in friction, the force required for angling the angle wire 101a also increases.

If an increase in the force required for angling the angle wire 101a can be detected in relation to a change in the bending characteristic, such a force increase can be used for varying the centering parameters. When the bendable portion 4a2 is bent, power is applied to the motor sections 55a2 and 55b2, and the sprockets 58a and 58b are rotated for a bending operation. As can be seen from this, the current values supplied to the motor sections 55a2 and 55b2 increase when the force required for angling the angle wire 101a increases.

In the fifth embodiment, the current sensing section 151 senses the current value of the motor sections 55a2 and 55b2 of the electric bending device 51. When the current value sensed by the current sensing section 151 exceeds a predetermined setting value, the switch 135 switches between the two parameter storage sections 134a and 134b. As a result, it is possible to appropriately determine how the bendable portion 4a2 should be bent when it is returned to the neutral position, and an optimal centering operation is attained.

The centering parameter-changing volume 121 shown in FIG. 11 may be used in this embodiment. In this case, the centering parameter-changing volume 121 directly changes the values of the parameters of the parameter storage section 114 connected to the centering control section 113 of the microcomputer 107, when the current value detected by the current sensing section 151 has exceeded the predetermined setting value.

The force required for angling angle wires may be detected based on a voltage, not a current. In this case, a voltage sensing section is provided to detect a voltage value applied to the motor sections 55a2 and 55b2. The motor sections 55a2 and 55b2 are driven powerfully by increasing the voltage value, so that a high voltage value indicates an increase in the force required for angling angle wires. When the voltage value sensed by the voltage sensing section exceeds a predetermined setting value, the switch 135 switches between the two parameter storage sections 134a and 134b.

Figure 18:
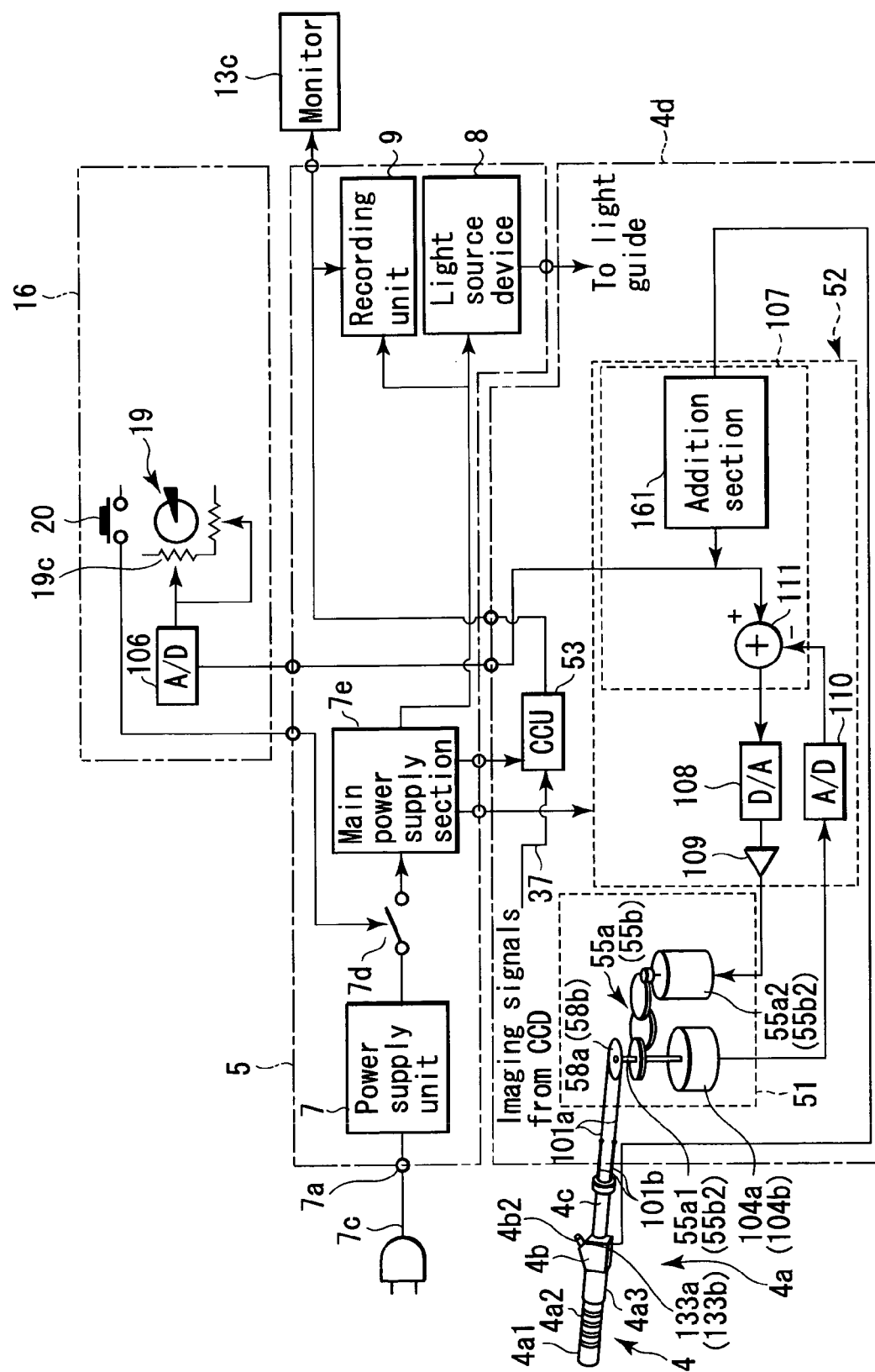
FIG. 18 is a schematic diagram illustrating the entire control circuit of an industrial endoscope apparatus according to the sixth embodiment of the present invention.

FIG. 18 shows the sixth embodiment of the present invention. The sixth embodiment differs from the first embodiment (FIGS. 1 through 10) in that the endoscope apparatus 1 is modified as follows:

Like the third embodiment (FIG. 12 through FIGS. 15A–15D), the sixth embodiment employs photo-couplers 133a and 133b as a recognition means 132 for recognizing forceps 131. The photo-couplers 133a and 133b are located at the channel port 4b2 of the intermediate coupler 4b of the scope section 4.

As shown in FIG. 18, the microcomputer 107 of the electric bending controller 52 is provided with an addition section 161 that adds digital signals on the basis of results of recognition of the recognition means 132. When the photo-couplers 133a and 133b sense forceps 131, the addition section 161 adds digital signals to the signals output from the A/D conversion section 106 of the remote control 16. As a result, an instruction for bending the bendable portion 4a2 more than the instruction entered from the joystick 19 is generated, and the generated instruction is supplied to the differential operation section 111.

Let us assume that the joystick 19 is moved upward when the bendable portion 4a2 is linear. In this case, the A/D conversion section 106 of the remote control 16 outputs digital signal "300." Since the A/D conversion section 110 outputs "512" then, a normal bending operation corresponds to (300–512). If the photo-couplers 133a and 133b recognize the forceps 131, the addition section 161 adds a predetermined value α (e.g., "20" in this case).

That is, the bendable portion 4a2 is bent by (280–512). When the bendable portion 4a2 is used in combination with the forceps 131, it cannot be easily bent. This is compensated for by adding the predetermined value α mentioned above.

The value of α varies depending upon the types of forceps 131. Therefore, if the photo-couplers 133a and 133b are configured to identify a number of types of forceps 131, the addition section 161 can prepare different values as α and add them based on the types identified.

The recognition means 132 for recognizing the forceps 131 is not limited to the photo-couplers and may be configured in the manner described in relation to the third embodiment.

In the sixth embodiment as well, not only the internal channel but also the external channel described above is applicable. Where the external channel is provided, the recognition means may be configured to recognize it, or forceps that are inserted into it.

The sixth embodiment may be modified to detect not only the presence/absence of the channel or forceps but also a state of the insertion section 4a of the scope section 4, as in the fifth embodiment shown in FIG. 17. Where the state of the insertion section is recognized, the addition section 161 adds digital values in such a manner as to increase the bending angle.

Moreover, the digital signal addition means is not limited to the addition section 161 described above. It may be an addition section configured to multiply an output of the D/A converter 108 by a predetermined coefficient, or an addition section configured to enhance the amplification function of the amplifier 109.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
a flexible insertion section which is insertable into a space to be inspected, the insertion section including a bendable portion at a distal end thereof;
a bending mechanism located on a proximal side of the insertion section, the bending mechanism being configured to drive the bendable portion;
a centering control section configured to control the bending mechanism such that the bendable portion is returned to a neutral position where the bendable portion is substantially linear;
a centering instruction input section from which an instruction for controlling the centering control section is input;
a recognition section configured to recognize a bending characteristic variance in each of directions in which the bendable portion is bendable;
a parameter storage section configured to store parameters for use in generating a centering instruction signal is generated based on an amount of bending of the bendable portion which varies in accordance with the bending characteristic variance in each of the directions; and
a bend-varying section configured to vary, in accordance with any of the parameters stored in the parameter storage section, the amount of bending of the bendable portion, which is performed when a bent state of the bendable portion is returned to a neutral position by the centering control section on the basis of a recognition result of the recognition section.

2. An endoscope according to claim 1, wherein:
a centering input section is connected to the centering control section; and
responsive to an operation by an operator, the centering input section outputs an instruction to generate a centering instruction signal and supplies the centering instruction signal to the centering control section on the basis of a centering parameter stored in the parameter storage section.

3. An endoscope according to claim 2, wherein:
the bending mechanism includes an operation section;
the operation section includes a remote control; and
the remote control includes a bend instruction section configured to designate a position and a direction in accordance with which the bendable portion should be bent.

4. An endoscope according to claim 3, wherein the bend instruction section is a joystick.

5. An endoscope according to claim 1, wherein:
the bend-varying section includes a parameter changing section;
the parameter changing section is connected to the centering control section, and directly changes the parameters in the parameter storage section such that the amount of bending of the bendable portion, which is performed when the bent state of the bendable portion is returned to the neutral position, is varied in accordance with the bending characteristic variance in each bending direction, the personal computer increasing those parameters corresponding to directions in which the bendable portion can hardly restore an original shape.

6. An endoscope according to claim 1, wherein:
the bend-varying section includes two parameter storage sections that store different centering parameters as data representing how the bendable portion should operate when the bendable portion is bent in each bending direction and is subject to a centering operation;
the two parameter storage sections include a first parameter storage section and a second parameter storage section;
the bend-varying section further includes a switch section interposed between the centering control section and the two parameter storage sections;
the first parameter storage section stores data representing how the bendable portion should operate in each bending direction where a treatment device is not inserted in a channel;
the second parameter storage section stores data representing how the bendable portion should operate in each bending direction where the treatment device is inserted in the channel;
the switch section operates on the basis of whether or not the treatment device is inserted into the channel, and switches the first and second parameter storage sections from one to another so as to perform a centering operation.

7. An endoscope comprising:
a flexible insertion section which is insertable into a space to be inspected, the insertion section including a bendable portion at a distal end thereof;
a bending mechanism located on a proximal side of the insertion section, the bending mechanism being configured to drive the bendable portion;
a recognition section configured to recognize a bending characteristic variance the bendable portion may undergo in each bending direction;
a parameter storage section stores configured to the parameters based on which a centering instruction signal is generated, the centering instruction signal corresponding to an amount of bending of the bendable portion, which varies in accordance with the bending characteristic variance in each bending direction; and
a bend-varying section configured to vary, in accordance with any of the parameters stored in the parameter storage section, an amount of bending of the bendable portion, which is performed when a bent state of the bendable portion is returned to a neutral position by the centering control section on the basis of a recognition result of the recognition section.

8. An endoscope according to claim 7, wherein the recognition section includes a determination section configured to determine whether or not the bending characteristic has varied by detecting whether or not there is a treatment device channel through which a treatment device is inserted into the insertion section.

9. An endoscope according to claim 7, wherein:
the insertion section includes an internal channel inside; and
the recognition section includes a treatment-device detector configured to detect whether or not a treatment device is inserted in the internal channel.

10. An endoscope according to claim 7, wherein the bend-varying section includes an addition section configured to add digital signals to control signals based on which the bendable portion is bent, the digital signals being added on the basis of a recognition result of the recognition section when the bending characteristic the bendable portion has for each bending direction varies.

11. An endoscope according to claim 8, wherein:
the insertion section includes an attachment portion to which an external channel for insertion of the treatment device is detachably attached;
the determination section includes an external channel detector configured to determine whether or not the external channel is attached to the attachment portion.

12. An endoscope according to claim 9, wherein the treatment-device detector includes a photo-coupler configured to determine whether or not the treatment device is inserted into the treatment device channel.

13. An endoscope according to claim 3, wherein the centering instruction input section includes a centering button located near the bend instruction section.

14. An endoscope according to claim 5, wherein the parameter changing section includes a personal computer.

15. An endoscope according to claim 5, wherein the parameter changing section includes a parameter-changing volume including a plurality of resistors.

16. An endoscope according to claim 6, wherein:
the insertion section includes an internal channel inside located therein; and
the recognition section includes a treatment-device detector configured to determine whether or not a treatment device is inserted in the internal channel.

17. An endoscope according to claim 3, wherein the treatment-device detector includes a photo-coupler.

18. An endoscope according to claim 9, wherein the bending mechanism includes operating wires configured to bend the bendable portion, and a driving motor configured to pull the operating wires.

19. An endoscope according to claim 18, wherein the recognition section includes a determination section configured to make a determination based on a current value of the driving motor.

20. An endoscope according to claim 18, wherein the recognition section includes a determination section configured to make a determination based on a voltage value of the driving motor.

21. An endoscope according to claim 11, wherein external channel detector includes a contact configured to detect the external channel.

* * * * *